United States Patent
Chi et al.

(10) Patent No.: US 9,751,844 B2
(45) Date of Patent: Sep. 5, 2017

(54) PRECURSOR COMPOUND CONNECTED TO SOLID SUPPORT FOR MANUFACTURING 18F RADIOPHARMACEUTICAL, METHOD FOR MANUFACTURING SAME, AND APPLICATION THEREOF

(75) Inventors: Dae-Yoon Chi, Seoul (KR); Byoung-Se Lee, Seoul (KR); Jae-Hak Lee, Incheon (KR); So-Young Chu, Seoul (KR); Woon-Jung Jung, Seoul (KR); Hye-Rim Kwon, Incheon (KR)

(73) Assignee: FUTURECHEM CO., LTD., Seoul (KR)

( * ) Notice: Subject to any disclaimer, the term of this patent is extended or adjusted under 35 U.S.C. 154(b) by 1086 days.

(21) Appl. No.: 13/994,339

(22) PCT Filed: Dec. 13, 2011

(86) PCT No.: PCT/KR2011/009571
§ 371 (c)(1),
(2), (4) Date: Jul. 18, 2013

(87) PCT Pub. No.: WO2012/081880
PCT Pub. Date: Jun. 21, 2012

(65) Prior Publication Data
US 2014/0011961 A1    Jan. 9, 2014

(30) Foreign Application Priority Data
Dec. 14, 2010  (KR) .................. 10-2010-0127934

(51) Int. Cl.
*A61K 9/00* (2006.01)
*C07D 249/04* (2006.01)
(Continued)

(52) U.S. Cl.
CPC ............ *C07D 249/04* (2013.01); *A61K 51/04* (2013.01); *A61K 51/0406* (2013.01);
(Continued)

(58) Field of Classification Search
CPC ................................... C07D 249/04
See application file for complete search history.

(56) References Cited

U.S. PATENT DOCUMENTS

2004/0236085 A1  11/2004  Luthra et al.
2008/0171863 A1   7/2008  Moon et al.
(Continued)

FOREIGN PATENT DOCUMENTS

CN        1246041        3/2006
GB    WO 03002157 A1 *  1/2003   ......... A61K 51/0491
(Continued)

OTHER PUBLICATIONS

Office Action for Chinese corresponding patent application No. 201180059657.X dated Nov. 4, 2014.
(Continued)

*Primary Examiner* — Paul Dickinson
(74) *Attorney, Agent, or Firm* — Renner, Otto, Boisselle & Sklar, LLP

(57) ABSTRACT

The present invention relates to a solid precursor in the form of an organic salt, the solid precursor having a solid support, a method for manufacturing same, and an application thereof. The solid precursor of the present invention enables omission of the [$^{18}$F]fluoride refining process using additional cartridge, and the use of excessive phase-transfer catalyst, and can easily remove remaining substance after reaction through the solid support inside the precursor. The solid precursor of the present invention is very appropriate for an automated synthesis device as an all-in-one system that can carry out overall process of [$^{18}$F]fluorosis reaction, when used by charging in a cartridge.

11 Claims, 3 Drawing Sheets

(51) Int. Cl.
| | |
|---|---|
| *A61K 51/04* | (2006.01) |
| *C07B 59/00* | (2006.01) |
| *C07C 229/60* | (2006.01) |
| *C07D 403/12* | (2006.01) |
| *C07D 417/14* | (2006.01) |
| *C07D 487/04* | (2006.01) |
| *C07H 19/06* | (2006.01) |
| *C08F 212/08* | (2006.01) |
| *C08F 212/14* | (2006.01) |
| *C08F 8/02* | (2006.01) |
| *C08F 8/30* | (2006.01) |
| *C08F 8/34* | (2006.01) |
| *C08F 8/44* | (2006.01) |
| *C08F 12/26* | (2006.01) |
| *C08F 12/30* | (2006.01) |
| *C08F 212/32* | (2006.01) |

(52) U.S. Cl.
CPC ........ *A61K 51/047* (2013.01); *A61K 51/0453* (2013.01); *A61K 51/0455* (2013.01); *A61K 51/0465* (2013.01); *A61K 51/0491* (2013.01); *C07B 59/00* (2013.01); *C07C 229/60* (2013.01); *C07D 403/12* (2013.01); *C07D 417/14* (2013.01); *C07D 487/04* (2013.01); *C07H 19/06* (2013.01); *C08F 8/02* (2013.01); *C08F 8/30* (2013.01); *C08F 8/34* (2013.01); *C08F 8/44* (2013.01); *C08F 212/08* (2013.01); *C08F 212/14* (2013.01); *C08F 12/26* (2013.01); *C08F 12/30* (2013.01); *C08F 212/32* (2013.01)

(56) References Cited

U.S. PATENT DOCUMENTS

| | | |
|---|---|---|
| 2010/0243972 A1 | 9/2010 | Voccia et al. |
| 2014/0046023 A1* | 2/2014 | Gottschall .......... B01D 15/3804 530/344 |

FOREIGN PATENT DOCUMENTS

| | | |
|---|---|---|
| WO | 2005/012319 | 2/2005 |
| WO | 2009/127372 | 10/2009 |
| WO | 2009/127372 A1 | 10/2009 |

OTHER PUBLICATIONS

IPRP for corresponding patent application No. PCT/KR2011/009571 dated Jun. 18, 2013.
International Search Report for corresponding patent application No. PCT/KR2011/009571 dated Jun. 19, 2012.
1M, S. "Ammonium Salt-Supported Precursors via Click Linkage for Simple Purification ofF-18 Labeled Compounds." M.Sc. Dissertation, Inha Univ. Feb. 28, 2010, pp. 15-16, 21-22, 26-32.
Sirion, U. et al. "Azide/Alkyne Resins for Quick Preparation of 1,4-Disubsituted 1,2,3-Triazoles." In: Bull. Kor. Chem. Soc., Jul. 31, 2010, vol. 31, pp. 1843-1847.
Brown, L. J. et al. "A Solid Phase Route to 18F-Labeled Tracers, Exemplified by the Synthesis of [18F]2-Fluoro-2-Deoxy-D-Glucose." In: Angew. Chem. Int. Ed., 2007, vol. 46, pp. 941-944.
Bejot, R. et al. "Fluorous Synthesis of 18F Radiotracers with the [18F]Fluoride Ion: Nucleophilic Fluorination as the Detagging Process." In: Angew. Chem. Int. Ed., 2009, vol. 48, pp. 586-589.

* cited by examiner

PRECURSOR COMPOUND CONNECTED TO SOLID SUPPORT FOR MANUFACTURING 18F RADIOPHARMACEUTICAL, METHOD FOR MANUFACTURING SAME, AND APPLICATION THEREOF

TECHNICAL FIELD

The present invention relates to a novel precursor for producing F-18 labeled [$^{18}$F]radiopharmaceuticals used in positron emission tomography, a method of manufacturing the same, and applications thereof.

BACKGROUND ART

Positron emission tomography (PET) is a nuclear molecular imaging technique for real-time imaging of the human body using a radiation tracker labeled with an isotope which emits positrons. Positron emission tomography can effectively detect biochemical and physiological changes in vivo occurring in the early stage of diseases and thus is showing the most rapid growth in medical imaging markets. Among a variety of positron-emitting nuclides obtainable using a cyclotron or a generator, F-18 (half-life=110 min) is undergoing thorough research and applications.

Methods of labeling an organic compound with F-18 may largely include an electrophilic substitution reaction and a nucleophilic substitution reaction. Particularly useful is a nucleophilic substitution reaction using [$^{18}$F]fluoride anions having high specific activity. Compared to other nucleophiles, an [$^{18}$F]fluoride nucleophile has lower reactivity, and may be subjected to a labeling reaction at a relatively high temperature and needs a comparatively large amount of precursor compound. The precursor means a compound having a leaving group which enables [$^{18}$F]fluoride to perform nucleophilic attack, that is, a compound having a leaving group instead of F-18 in an F-18 labeled compound. [$^{18}$F]Fluoride produced by a cyclotron is provided in the form of a metal salt in a state of being dissolved in an [$^{18}$O]H$_2$O aqueous solution, and a cartridge having an anion exchange resin is used to refine [$^{18}$F]fluoride and to remove an excess of water. When the [$^{18}$F]fluoride aqueous solution is allowed to flow to the cartridge, only the [$^{18}$F]fluoride is captured, and the other metal salt and water are removed. The [$^{18}$F]fluoride solution is eluted from the [$^{18}$F]fluoride-captured cartridge using an appropriate electrolyte solution. The eluted [$^{18}$F]fluoride solution contains a large amount of water, and a dewatering process is thus required, which is typically performed for 15~20 min. Because the half-life of F-18 is 110 min, the dewatering process results in a decrease in radiation dose of about 10%.

In order to increase reactivity of the [$^{18}$F]fluoride, various phase transfer catalysts have been used. Currently, kryptofix [2.2.2] is very useful. Although kryptofix is commercially available, it is very expensive and has high toxicity. Also, because the half-life of F-18 is short, a labeling reaction should be rapidly carried out to produce [$^{18}$F]radiopharmaceuticals in high yield. An excess of precursor is typically used to achieve a rapid labeling reaction, but the excess of precursor used is left as an impurity along with byproducts after the labeling reaction. Consequently, the purification process of [$^{18}$F]radiopharmaceuticals may become complicated or the purity of refined [$^{18}$F]radiopharmaceuticals may be lowered.

With the goal of effectively removing the reaction byproducts and unreacted precursor, some methods have been developed in which the structure of the sulfonate leaving group of the precursor is modified.

Specifically, it was reported that an insoluble polymer having a sulfonyl chloride functional group is used to synthesize a perfluoroalkyl sulfonate precursor supported to the polymer, which is then easily removed via filtration after the reaction (WO 2005/012319 A1; L, J. Brown, *Angew. Chem. Int. Ed.*, 46, 941-944, 2007). However, the preparation of the insoluble polymer having the perfluoroalkane sulfonyl chloride functional group is considerably complicated, and there is little analytical data for the polymer at individual steps, making it difficult to reproduce the above procedures. Further, most of the compounds after the reaction may be released from the polymer into a reaction solution due to the side reactions, and thus there is no effect for compound purification unlike original purposes.

Examples of the polymer developed to perform an F-18 labeling reaction to date include 1) an anion exchange resin for use in refining [$^{18}$F]fluoride from a metal salt aqueous solution, and 2) a polymer type precursor. In respective cases, polymer structures and purposes of use thereof are independent of each other.

The present inventors have paid attention to precursors having an organic salt which induces an intramolecular nucleophilic substitution reaction, and therefore have developed a solid precursor having an organic salt connected to a solid support and confirmed that such a precursor may refine [$^{18}$F]fluoride in an [$^{18}$F]fluoride aqueous solution, and also the organic salt acts as an intramolecular phase transfer catalyst so that on-resin or on-cartridge [$^{18}$F]fluorination may be carried out, thus culminating in the present invention.

DISCLOSURE

Technical Problem

An object of the present invention is to provide a solid precursor compound for use in manufacturing [$^{18}$F]radiopharmaceuticals.

Another object of the present invention is to provide a method of preparing the solid precursor.

Still another object of the present invention is to provide a cartridge filled with the solid precursor for use in [$^{18}$F]fluorination.

Yet another object of the present invention is to provide a method of manufacturing an [$^{18}$F]radiopharmaceutical using the cartridge filled with the solid precursor.

Technical Solution

In order to accomplish the above objects, the present invention provides a solid precursor compound represented by the following Chemical Formula 1.

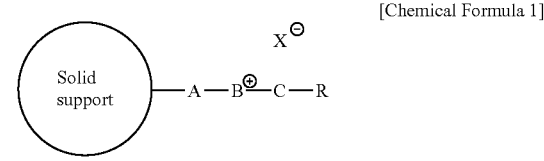

[Chemical Formula 1]

In Chemical Formula 1, a solid support, A, B, C, R and X are defined as in the specification.

Also, a method of preparing the solid precursor according to the present invention may be widely defined to the following Preparations 1 to 5.

(1) Preparation 1 is a method of preparing a solid precursor of Chemical Formula 1 by reacting a solid compound including a precursor with an alkylating reagent.

Preparation 1:

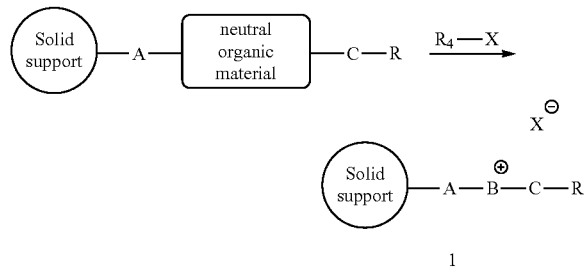

(2) Preparation 2 is a method of preparing a solid precursor of Chemical Formula 1 from a precursor monomer including an organic salt using a radical initiator.

Preparation 2:

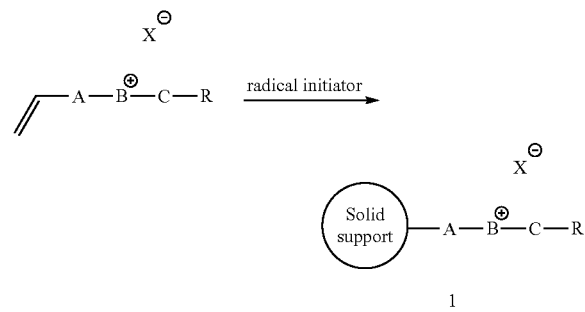

(3) Preparation 3 is a method of preparing a solid precursor of Chemical Formula 1 by reacting a solid compound having a leaving group with an alcohol compound (HO—R) including a precursor.

Preparation 3:

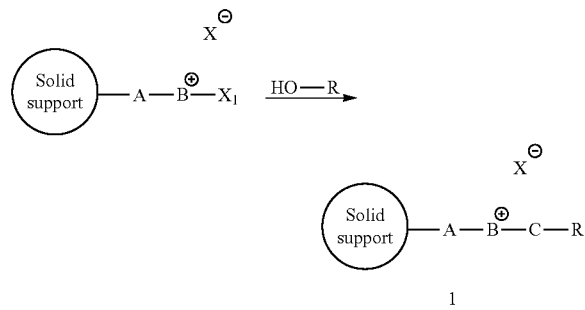

In Preparation 3, C of Chemical Formula 1 is oxygen.

(4) Preparation 4 is a method of preparing a solid precursor of Chemical Formula 1 by reacting a solid compound having a leaving group with a neutral organic material including a precursor.

Preparation 4:

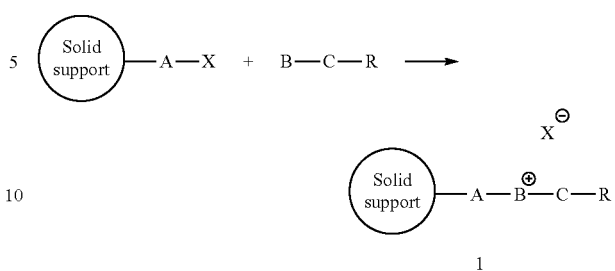

(5) Preparation 5 is a method of preparing a solid precursor of Chemical Formula 1 by reacting a solid compound having a neutral organic material with a precursor having a leaving group.

Preparation 5:

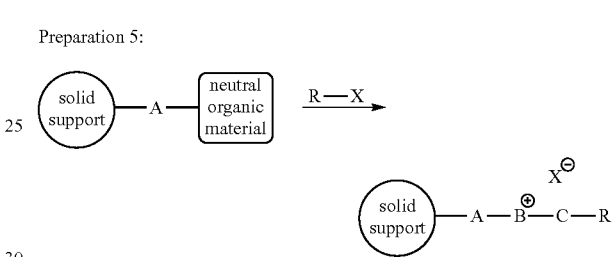

Further, the present invention provides a method of manufacturing an [$^{18}$F]radiopharmaceutical, comprising performing nucleophilic [$^{18}$F]fluorination using the solid precursor of Chemical Formula 1, as shown in the following Preparation 6.

Preparation 6:

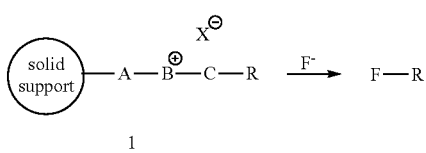

In Preparation 6, a solid support, A, B, C, R and X are defined as in the specification, and F is $^{18}$F.

Furthermore, the present invention provides a cartridge filled with the solid precursor of Chemical Formula 1.

In addition, the present invention provides a method of manufacturing an [$^{18}$F]radiopharmaceutical, comprising capturing an [$^{18}$F]fluoride ion from an [$^{18}$F]fluoride solution using a cartridge filled with a solid precursor represented by Chemical Formula 1 (Step 1); heating the cartridge including the captured [$^{18}$F]fluoride ion so that nucleophilic [$^{18}$F] fluorination is carried out in the cartridge (Step 2); and eluting the produced [$^{18}$F]radiopharmaceutical using a solvent and filtering it. As such, the present invention may further include performing deprotection under acidic or basic conditions after the nucleophilic [$^{18}$F]fluorination in the cartridge filled with the solid precursor of Chemical Formula 1.

Advantageous Effects

According to the present invention, an organic salt in a solid precursor plays a role as an anion exchange resin, so that an [$^{18}$F]fluoride ion can be captured using an ionic exchange method, thus obviating the need for an [$^{18}$F] fluoride refining process using an additional cartridge. Also, because the organic salt in the solid precursor according to the present invention functions as a phase transfer catalyst, there is no need for an excess of an additional phase transfer catalyst, and an intramolecular nucleophilic substitution reaction of the captured and activated [$^{18}$F]fluoride ion is induced by the organic salt functioning as the phase transfer catalyst, so that the reaction rate can increase, compared to a typical intermolecular nucleophilic substitution reaction. Furthermore, the remaining precursors after the reaction are coupled to the polymer, and can thus be easily removed. According to the present invention, the entire procedure of [$^{18}$F]radiopharmaceutical synthesis including [$^{18}$F]fluoride anion capture, nucleophilic [$^{18}$F] fluorination, and purifying can be conducted in the same cartridge, thus remarkably simplifying an automated synthesis process of [$^{18}$F]radiopharmaceuticals.

MODE FOR INVENTION

Figure 1:
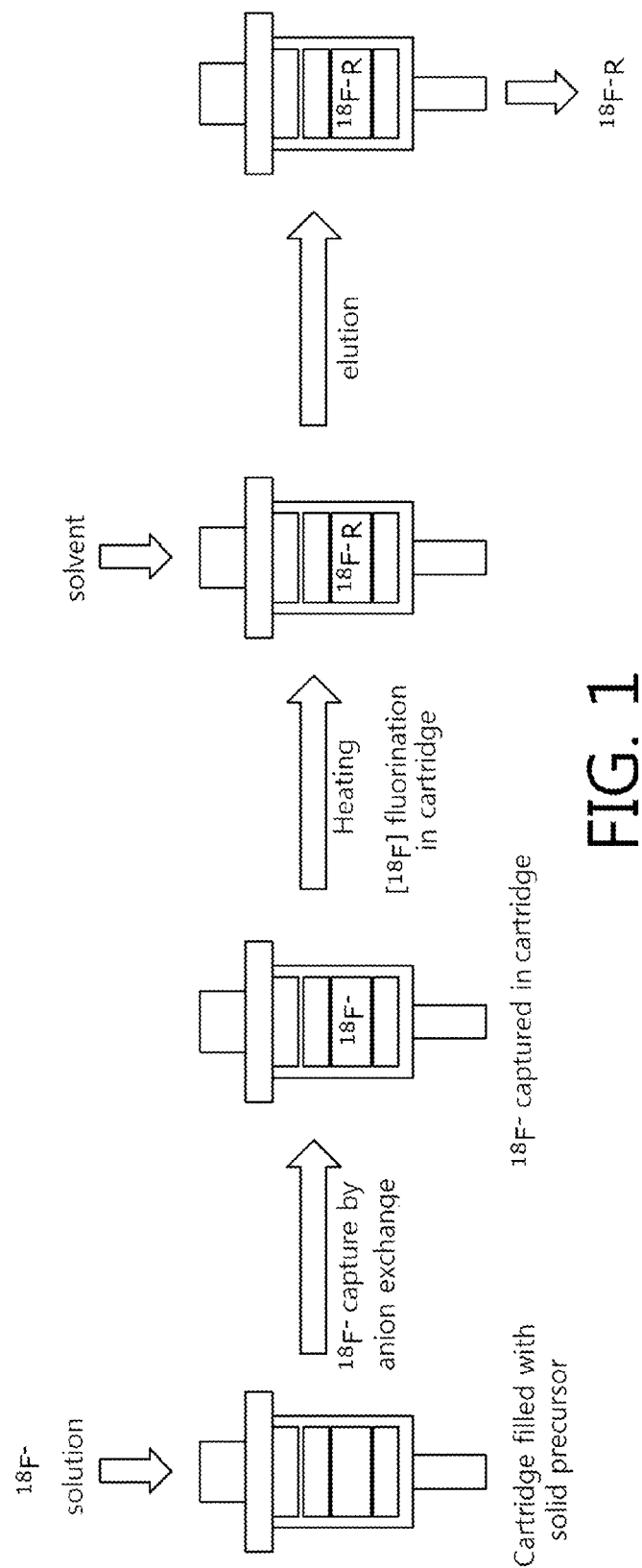
FIG. 1 schematically illustrates capturing of an [$^{18}$F] fluoride anion using a cartridge filled with a solid precursor of Chemical Formula 1 according to the present invention, and [$^{18}$F] fluorination in the cartridge.
Figure 2:
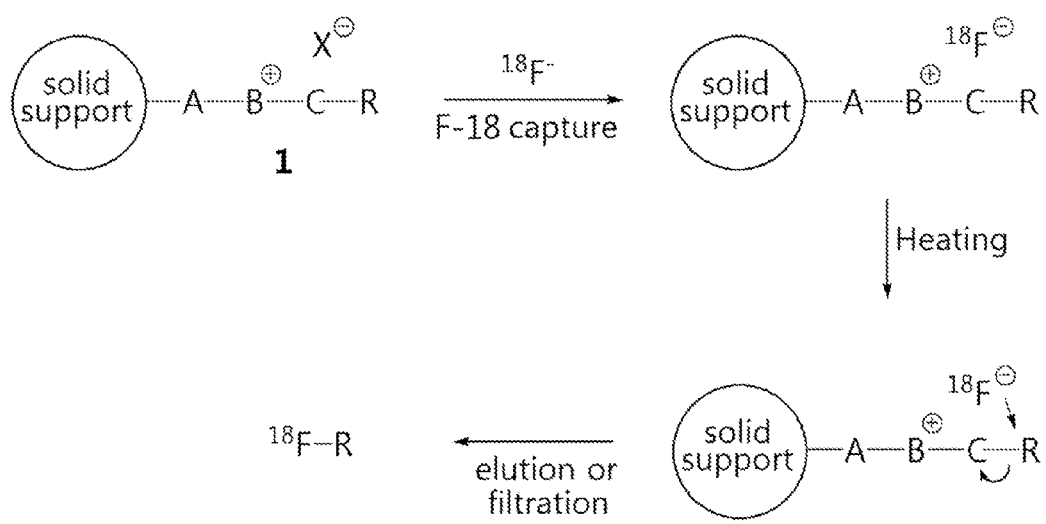
FIG. 2 schematically illustrates capturing of an [$^{18}$F] fluoride anion and intramolecular [$^{18}$F] fluorination, using the solid precursor of Chemical Formula 1 according to the present invention.

Hereinafter, a detailed description will be given of the present invention.

The present invention provides a solid precursor represented by Chemical Formula 1 below.

[Chemical Formula 1]

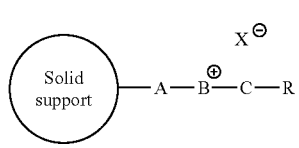

In Chemical Formula 1, a solid support is an insoluble organic polymer or an insoluble inorganic oxide, A is a linker, B is an organic cation, C is a single bond, —O— or -D-SO$_2$—O—, wherein D is a single bond or a C$_{1-30}$ hydrocarbon group, and the hydrocarbon group may include one or more selected from the group consisting of nitrogen, oxygen and sulfur and is unsubstituted or substituted with a halogen, R is an organic group other than F-18 in an [$^{18}$F]labeled radiopharmaceutical, and hydrogen in the organic group is unsubstituted or substituted with a protecting group, and X is an anion.

In the present invention, the hydrocarbon group indicates any organic group composed of carbon and hydrogen, and the organic group may have any known structure such as an alkyl group, an alkenyl group, an alkynyl group, an aryl group, an aralkyl group, a heteroaryl group, etc. One or more heteroatoms such as nitrogen, oxygen, sulfur or phosphorus may be interposed between carbons of the hydrocarbon according to the present invention, and hydrogen of the hydrocarbon according to the present invention may be substituted with a halogen such as fluorine, chlorine, bromine, and iodine.

In the present invention, the linker A includes any known organic group adapted to sufficiently space the reactive portion from the solid support structure to maximize reactivity.

In the present invention, R includes a portion other than F-18 in any known structure of "F-18 labeled radiopharmaceuticals for use in positron emission tomography," and R may include a protecting group. The protecting group is a substituent which temporarily protects a functional group having high reactivity, and includes any substituent known in the art. Examples thereof include alkoxy (—OR), alkoxycarbonyl (—C(O)OR), triphenylmethyl (—C(Ph)$_3$), alkoxymethyl (—CH$_2$OR), acyl (—C(O)R), silyl (—SiRiR$_2$R$_3$), benzyl (—CH$_2$Ph), tetrahydropyranyl (-THP), allyl (—CH$_2$CH=CH$_2$), etc.

Preferably, R is

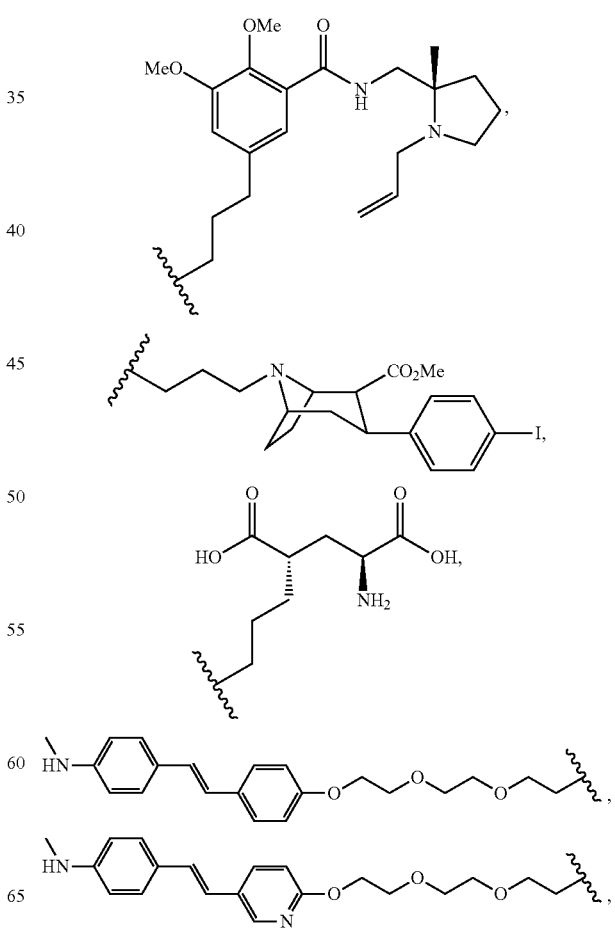

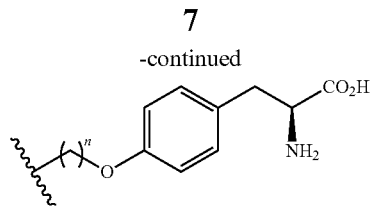

(wherein n is an integer of 1~5)

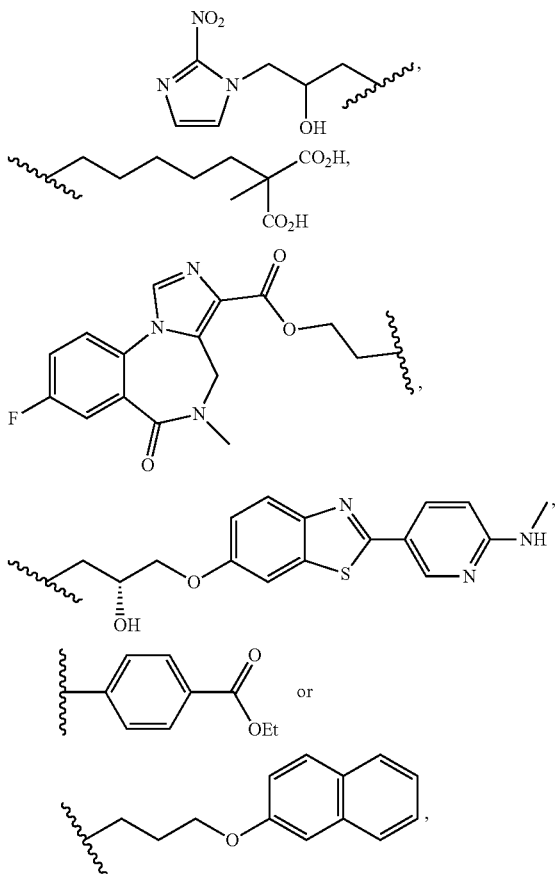

wherein the hydrogen is unsubstituted or substituted with a protecting group.

Preferably, the solid support is an insoluble organic polymer selected from the group consisting of polystyrene, polyacrylic acid, polyacrylate, polyacrylamide, polyacrylonitrile, polyethyleneglycol, polyester, polyethylene, polypropylene, polyvinylalcohol, polyethyleneimine, polymethylene oxide, cellulose and mixtures thereof, or is an insoluble inorganic oxide selected from the group consisting of silica, aluminum oxide, titanium oxide and zeolite, A is a $C_{1-30}$ hydrocarbon group, and the hydrocarbon group may include one or more selected from the group consisting of nitrogen, oxygen and sulfur and is unsubstituted or substituted with a halogen, B is a $C_1$-$C_{100}$ organic cation which contains a heteroatom selected from the group consisting of oxygen, nitrogen, sulfur, phosphorus and combinations thereof and is unsubstituted or substituted with a halogen, and preferably B is

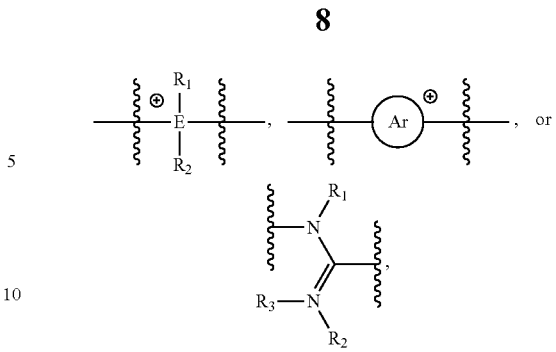

wherein E is nitrogen or phosphorus, and $R_1$, $R_2$ and $R_3$ are the same as or different from each other and are a $C_1$-$C_{20}$ hydrocarbon group, and the hydrocarbon group may include one or more selected from the group consisting of nitrogen, oxygen and sulfur and is unsubstituted or substituted with a halogen, Ar is a $C_2$-$C_{20}$ heteroaromatic cation containing one or more nitrogens, nitrogen and oxygen, or nitrogen and sulfur, and is connected with a linker at one nitrogen position or is substituted with a $C_1$-$C_{20}$ hydrocarbon group, and the hydrocarbon group may include one or more selected from the group consisting of nitrogen, oxygen and sulfur and is unsubstituted or substituted with a halogen, R is a $C_1$-$C_{1000}$ hydrocarbon group, and the hydrocarbon group may include one or more selected from the group consisting of nitrogen, oxygen and sulfur and is unsubstituted or substituted with a halogen, and X is tetrafluoroborate ($BF_6$), hexafluorophosphate ($PF_6$), hexafluoroantimonate ($SbF_6$), bis(trifluoromethane) sulfonimide ($N(Tf)_2$), nitrate ($NO_3$), sodium sulfate ($NaSO_4$), sodium carbonate ($KCO_3$), sodium bicarbonate ($HCO_3$), potassium phosphate ($KHPO_4$ or $K_2PO_4$), alkane carboxylate ($R'CO_2$) or alkane sulfonate ($R'SO_3$), wherein R' is a $C_{1-50}$ hydrocarbon group, and the $C_{1-50}$ hydrocarbon group may include one or more selected from the group consisting of nitrogen, oxygen, sulfur, phosphorus and combinations thereof and is unsubstituted or substituted with a halogen.

More preferably, the solid support is an insoluble organic polymer selected from the group consisting of polystyrene, polyacrylate, polyacrylamide, polyacrylonitrile, polyethyleneglycol and mixtures thereof, A is $—CH_2—O—CH_2—$,

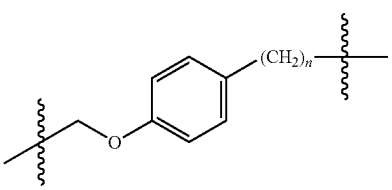

or $—(CH_2)_n—$, wherein n is 1~12,

B is

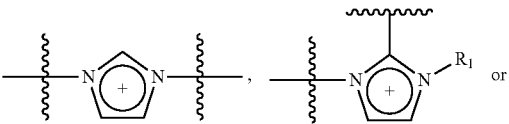

-continued

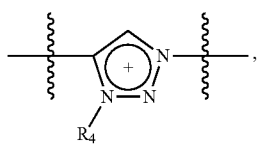

wherein $R_4$ is a $C_1$-$C_{10}$ alkyl group,

C is a single bond, —O—, or -D-$SO_2$—O—, wherein D is —$(CH_2)_n$— (n is 1~3) or

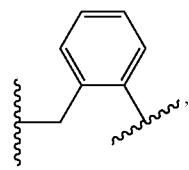

and

X is methanesulfonate, trifluoromethanesulfonate, or p-nitrobenzenesulfonate.

According to an embodiment of the present invention, the precursor represented by Chemical Formula 1 may include precursors shown by the following chemical formulas.

[Chemical Formula 1-1]

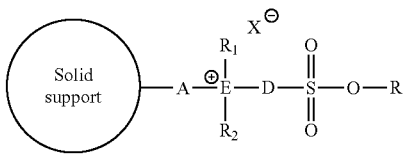

The solid support, A, D, R, Ar and X are defined as above.

[Chemical Formula 1-2]

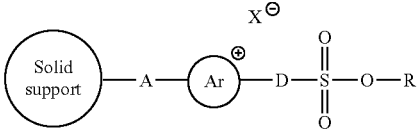

The solid support, A, D, R, Ar and X are defined as above.

[Chemical Formula 1-3]

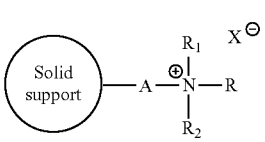

The solid support, A, R, $R_1$, $R_2$ and X are defined as above.

[Chemical Formula 1-4]

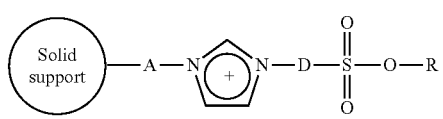

The solid support, A, R, $R_1$, $R_2$, $R_3$ and X are defined as above.

Particularly, the compound represented by Chemical Formula 1-2 may include precursors shown by the following chemical formulas.

[Chemical Formula 1-2a]

[Chemical Formula 1-2b]

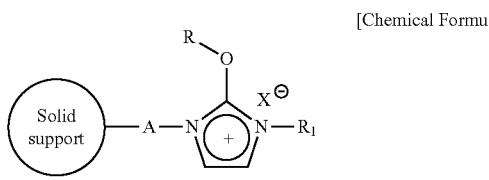

[Chemical Formula 1-2c]

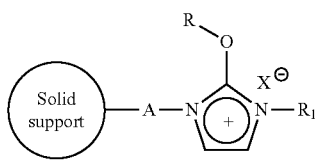

In Chemical Formulas 1-2a, 1-2b and 1-2c, the solid support, A, D, R, $R_1$ and X are defined as above, and $R_4$ is a $C_{1-10}$ alkyl group.

Also, the present invention provides a method of preparing a solid precursor represented by Chemical Formula 1-2a, as shown in Schemes 1 to 3 below.

Specifically, the present invention provides a method of preparing a solid precursor represented by Chemical Formula 1-2a, as shown in the following Scheme 1, comprising subjecting a solid support having a terminal alkyne group represented by Chemical Formula 2 and an azidoalkane sulfonate compound represented by Chemical Formula 3 to an alkyne/azide [3+2] cycloaddition reaction in the presence of a copper (I) catalyst, thus preparing a compound connected to a solid support having a 1,2,3-triazole group represented by Chemical Formula 4 (Step 1); and subjecting 1,2,3-triazole of the compound connected to the solid support represented by Chemical Formula 4 obtained in Step 1 to alkylation, thus preparing a solid precursor having a 1,2,3-triazolium salt (Step 2).

[Scheme 1]

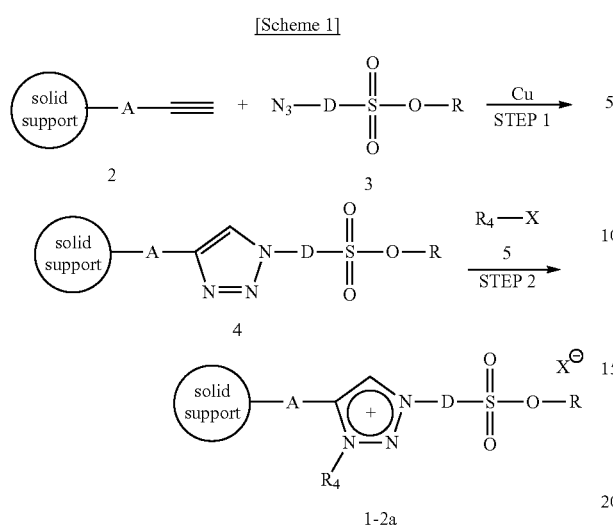

In Scheme 1, the solid support, A, D, X, R and R$_4$ are defined as above.

Specifically, the present invention provides a method of preparing a solid precursor represented by Chemical Formula 1-2a, as shown in the following Scheme 2, comprising subjecting a 1,2,3-triazole sulfonate compound represented by Chemical Formula 6 to radical polymerization in the presence of a cross-linker and a radical initiator, thus preparing a compound connected to a solid support having a 1,2,3-triazole group represented by Chemical Formula 4 (Step 1); and subjecting 1,2,3-triazole of the compound connected to the solid support represented by Chemical Formula 4 obtained in Step 1 to alkylation, thus preparing a solid precursor having a 1,2,3-triazolium salt (Step 2).

[Scheme 2]

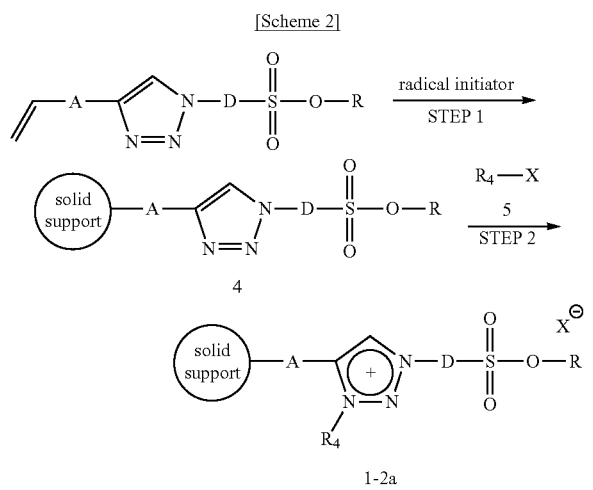

In Scheme 2, the solid support, A, D, X, R and R$_4$ are defined as above.

Specifically, the present invention provides a method of preparing a solid precursor compound represented by Chemical Formula 1-2a, as shown in the following Scheme 3, comprising subjecting a 1,2,3-triazole sulfonate compound represented by Chemical Formula 6 to alkylation, thus synthesizing a compound represented by Chemical Formula 7 having a 1,2,3-triazolium salt (Step 1); and subjecting the 1,2,3-triazolium sulfonate compound by Chemical Formula 7 obtained in Step 1 to radical polymerization in the presence of a cross-linker and a radical initiator, thus preparing a solid precursor having a 1,2,3-triazolium salt (Step 2).

[Scheme 3]

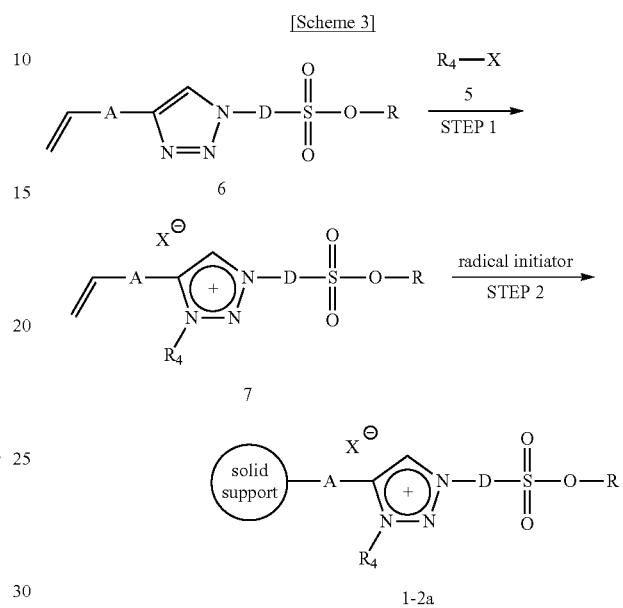

In Scheme 3, the solid support, A, D, X, R and R$_4$ are defined as above.

Also, the present invention provides a method of preparing a solid precursor compound represented by Chemical Formula 1-2b, as shown in the following Scheme 4, comprising reacting an imidazolium sulfonate solid compound represented by Chemical Formula 8 with an acid, thus synthesizing an imidazolium sulfonic acid solid compound represented by Chemical Formula 9 (Step 1); treating the solid compound represented by Chemical Formula 9 obtained in Step 1 with thionyl chloride (SOCl$_2$), thus synthesizing an imidazolium sulfonyl chloride solid compound represented by Chemical Formula 10 (Step 2); and reacting the solid compound represented by Chemical Formula 10 obtained in Step 2 with an alcohol compound represented by Chemical Formula 11, thus preparing a solid precursor having an imidazolium salt (Step 3).

[Scheme 4]

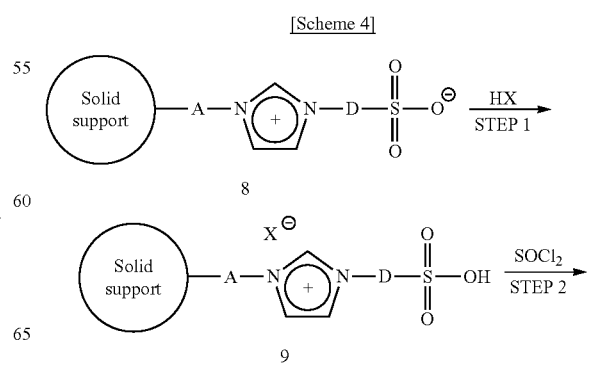

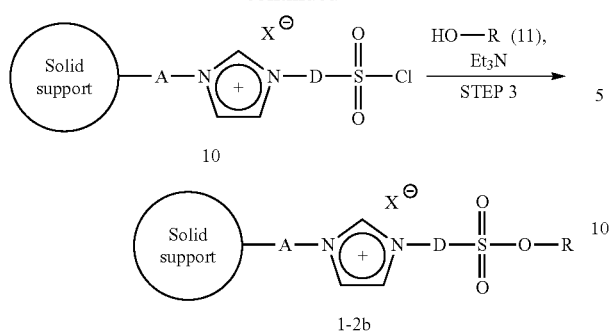

1-2b

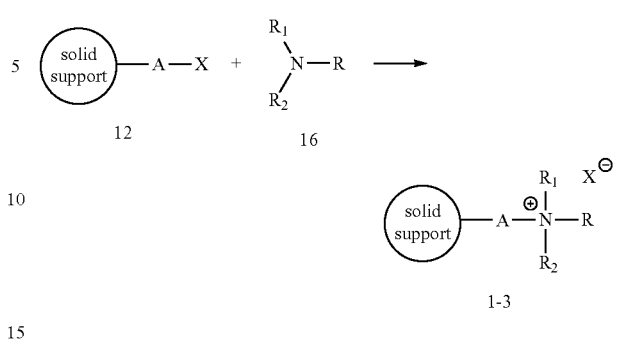

1-3

In Scheme 4, the solid support, A, D, X and R are defined as above.

Also, the present invention provides a method of preparing a solid precursor compound represented by Chemical Formula 1-2c, as shown in the following Scheme 5, comprising reacting a solid compound represented by Chemical Formula 12 with a 2-imidazolone compound represented by Chemical Formula 13 under basic conditions, thus synthesizing a solid compound represented by Chemical Formula 14 (Step 1); and adding the solid compound represented by Chemical Formula 14 obtained in Step 1 with a compound represented by Chemical Formula 15, thus preparing a solid precursor having an imidazolium salt (Step 2).

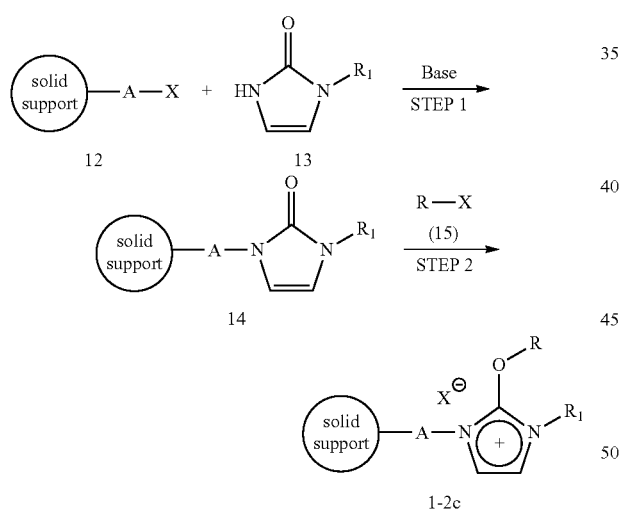

1-2c

In Scheme 5, the solid support, A, R, $R_1$ and X are defined as above.

Also, the present invention provides a method of preparing a solid precursor represented by Chemical Formula 1-3, as shown in Scheme 6 below.

Specifically, the present invention provides a method of preparing a solid precursor compound represented by Chemical Formula 1-3, as shown in the following Scheme 6, comprising adding a solid compound represented by Chemical Formula 12 with a tertiary amine represented by Chemical Formula 16, thus preparing a solid precursor of Chemical Formula 1-3.

In Scheme 6, the solid support, A, R, $R_1$, $R_2$ and X are defined as above.

In Schemes 1 to 6, the starting materials are commercially available or may be directly synthesized materials. Also, the solvent participating in individual reactions may be appropriately selected by those skilled in the art, and is preferably selected from the group consisting of tetrahydrofuran, 1,4-dioxane, dichloromethane, chloroform, carbon tetrachloride, 1,2-dichloroethane, benzene, toluene, acetonitrile, N,N-dimethylformamide, dimethylsulfoxide, methanol, ethanol, isopropanol, t-butanol, water, and solvent mixtures thereof.

The copper catalyst may include a copper (I) catalyst such as CuI, CuBr, CuCl, etc., or a copper (II) catalyst, such as $CuSO_4$, $Cu(OAc)_2$, $Cu(NO_3)_2$, $Cu(OTf)_2$, CuO, etc. In the case where the oxidation state of the copper catalyst is 1, a base such as an alkali metal salt of a bicarbonate ion, an alkali metal salt of a carbonate ion, or triethylamine, diisopropylethylamine, pyridine, rutidine, cholidine, etc., may be additionally used. In the case where the oxidation state of the copper catalyst is 2, a reducing agent such as sodium ascorbate, sodium sulfite ($Na_2SO_3$), dithiothreitol, etc., may be additionally used.

Also, the radical initiator is typically used upon synthesis of a radical polymer, and may include any radical initiator widely known to those skilled in the field of polymer synthesis.

Specifically, the present invention provides a method of manufacturing an [$^{18}$F]radiopharmaceutical, as shown in the following Scheme 7, comprising performing nucleophilic [$^{18}$F]fluorination using the solid precursor of Chemical Formula 1.

[Scheme 7]

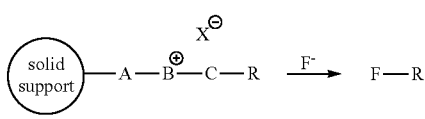

1

In Scheme 7, the solid support, A, B, C, R and X are defined as above, and F is $^{18}$F.

According to the present invention, an F-18 labeling method (Scheme 7) using the solid precursor of Chemical Formula 1 may be performed using a labeling method in any reactor widely known to those skilled in the F-18 labeling field. Also, the method according to the present invention may be effectively performed with a labeling method in a cartridge. Specifically, the method of manufacturing the [$^{18}$F]radiopharmaceutical according to the present invention comprises capturing an [¹⁸F]fluoride ion from an [¹⁸F] fluoride ion-dissolved solution using a cartridge filled with the solid precursor represented by Chemical Formula 1; heating the cartridge having the captured [¹⁸F]fluoride ion so that nucleophilic [¹⁸F]fluorination is carried out in the cartridge; and eluting the produced [¹⁸F]radiopharmaceutical using a solvent and filtering it. The method of manufacturing the [¹⁸F]radiopharmaceutical using the cartridge filled with the solid precursor represented by Chemical Formula 1 according to an embodiment of the present invention is illustratively shown in FIG. 1. The method using the solid precursor according to the present invention is a system in which the entire procedure of the nucleophilic [¹⁸F]fluorination may be carried out in the cartridge, and is very adaptable for an automated synthesis device.

Figure 3:
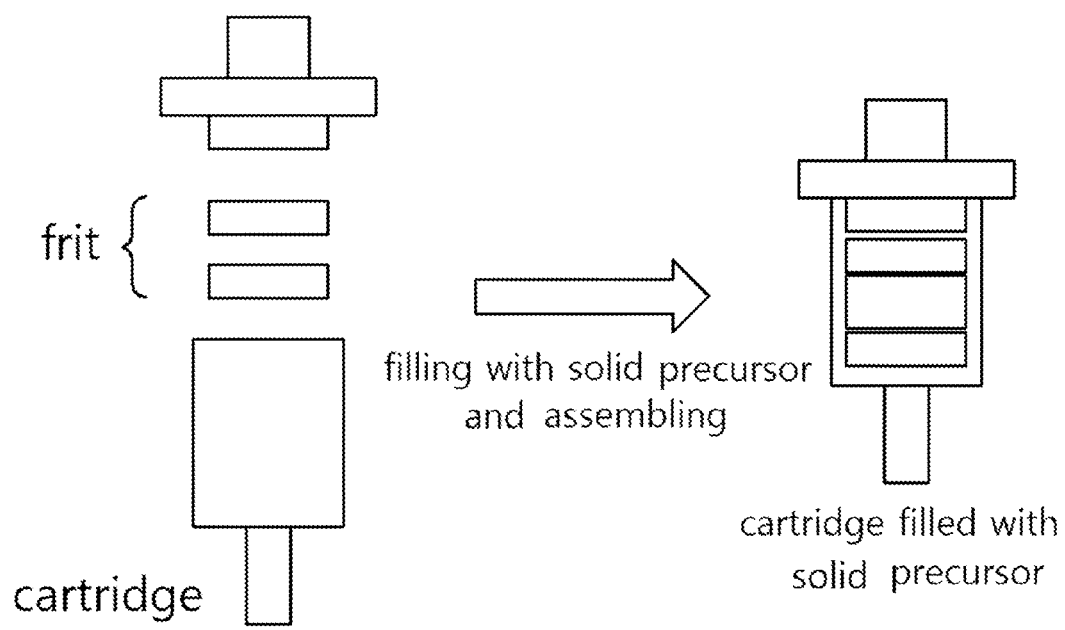
FIG. 3 schematically illustrates the cartridge filled with the solid precursor of Chemical Formula 1 according to the present invention and a manufacturing process thereof.

Further, the present invention provides a cartridge for [¹⁸F]fluorination, which is filled with the solid precursor represented by Chemical Formula 1 according to the present invention. The method of manufacturing the cartridge for use in producing [¹⁸F]radiopharmaceuticals is widely known to those skilled in the art, and a detailed description thereof is omitted. For reference, the cartridge according to an embodiment of the present invention is illustrated in FIG. 3.

A better understanding of the present invention may be obtained via the following preparation examples and examples, which are set forth to illustrate, but are not to be construed as limiting, the present invention.

<Preparation Example 1> Preparation of 4-vinylbenzyl propargyl ether (19)

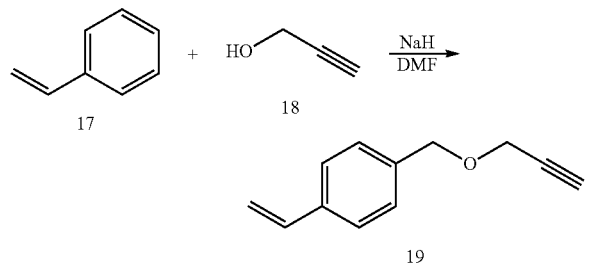

Anhydrous dimethylformamide (150.0 mL) was placed in a reactor containing 60% sodium hydride (NaH, 2.13 g, 53.22 mmol) under nitrogen, and propargyl alcohol (18, 2.48 mL, 42.58 mmol) was added at 0° C., after which the resulting mixture was stirred at 0° C. for 30 min. 4-vinylbenzyl chloride (17, 5.00 mL, 35.48 mmol) was slowly added, and the resulting mixture was stirred for 3 hr from 0° C. to room temperature, and the reaction was terminated with 2N hydrochloric acid. The organic compound was extracted with ethylacetate, and the organic layer was dewatered using anhydrous sodium sulfate and then subjected to column chromatography (5% ethylacetate/n-hexane), thus obtaining a desired compound, that is, 4-vinylbenzyl progargyl ether (19, 4.34 g, 71%).

¹H NMR (500 MHz, CDCl₃) δ 2.49 (t, J=2.5 Hz, 1H), 4.19 (d, J=2.0 Hz, 1H), 4.62 (s, 2H), 5.27 (d, J=10.5 Hz, 2H), 5.78 (d, J=18.0 Hz, 1H), 6.74 (dd, J=17.8, 10.8 Hz, 1H), 7.34 (d, J=8.5 Hz, 2H), 7.42 (d, J=8.0 Hz, 2H)

¹³C NMR (125 MHz, CDCl₃) δ 57.3, 71.5, 74.9, 79.9, 114.3, 126.6, 128.6, 136.7, 137.1, 137.5

<Preparation Example 2> Preparation of 3-(2-naphthoxy)propyl 3-azidopropane sulfonate (3a)

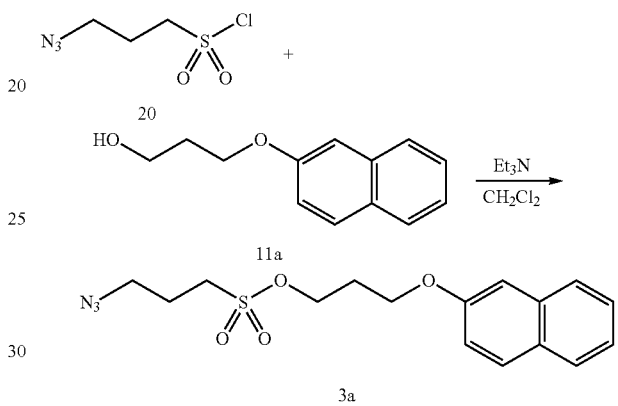

2-(3-hydroxypropoxy)naphthalene (11a, 1.00 mg, 4.944 mmol) and 3-azidopropanesulfonyl chloride (20, 999 mg, 5.439 mmol) were dissolved in dichloromethane (40 mL), and triethylamine (0.91 mL, 6.427 mmol) was slowly added at 0° C., after which the resulting mixture was stirred at 0° C. for 1 hr. The reaction was terminated with water, and the organic compound was extracted with dichloromethane. The extracted dichloromethane solution was treated with anhydrous sodium sulfate and then subjected to column chromatography (40% ethylacetate/n-hexane), thus obtaining a desired compound, that is, 3-(2-naphthoxy)propyl 3-azidopropane sulfonate (3a, 1.676 g, 97%).

¹H NMR (500 MHz, CDCl₃) δ 2.07 (quintet, J=6.8 Hz, 2H), 2.31 (quintet, J=5.9 Hz, 2H), 3.19 (t, J=7.3 Hz, 2H), 3.41 (t, J=6.3 Hz, 2H), 4.22 (t, J=5.8 Hz, 2H), 4.51 (t, J=6.0 Hz, 2H), 7.15-7.16 (m, 2H), 7.37 (t, J=7.5 Hz, 1H), 7.47 (t, J=7.5 Hz, 1H), 7.74-7.80 (m, 3H)

¹³C NMR (125 MHz, CDCl₃) δ 23.6, 29.3, 47.4, 49.3, 63.3, 67.0, 106.8, 118.8, 124.0, 126.7, 126.9, 127.8, 129.2, 129.7, 134.6, 156.5

<Preparation Example 3> Preparation of Compound 6a

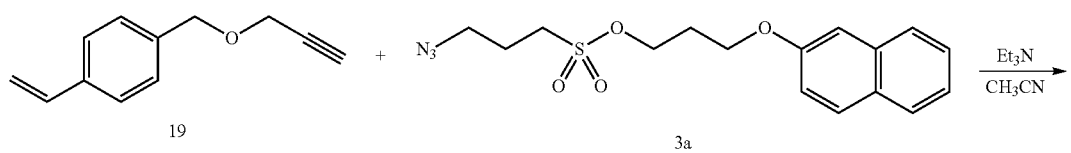

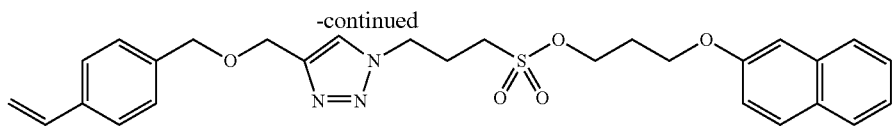

6a 4-vinylbenzyl propargyl ether (19, 3.00 g, 15.62 mmol) obtained in Preparation Example 1 and the azido compound (3a, 6.09 g, 15.62 mmol) obtained in Preparation Example 2 were dissolved in acetonitrile (300 mL), and copper iodide (149 mg, 0.781 mmol) and triethylamine (0.11 mL, 0.781 mmol) were sequentially added, after which the resulting mixture was reacted at room temperature for 6 hr. Acetonitrile was removed under reduced pressure, the reaction mixture was dissolved in ethylacetate, and water was added, after which the organic layer was separated. The water layer was extracted with ethylacetate, and the separated organic layer was treated with anhydrous sodium sulfate and then subjected to column chromatography (50% ethylacetate/n-hexane), thus obtaining a desired compound 6a (8.36 g, 92%).

$^1$H NMR (500 MHz, CDCl$_3$) δ 2.27 (quintet, J=5.88 Hz, 2H), 2.43 (quintet, J=6.88 Hz, 5H), 3.11 (t, J=7.0 Hz, 2H), 4.19 (t, J=5.8 Hz, 2H), 4.43 (t, J=6.5 Hz, 2H), 4.48 (t, J=6.0 Hz, 2H), 4.58 (s, 2H), 4.63 (s, 2H), 5.24 (d, J=10.5 Hz, 1H), 5.74 (dd, J=17.5, 0.5 Hz, 1H), 6.70 (dd, J=17.5, 11.0 Hz, 7.10-7.13 (m, 2H), 7.30-7.35 (m, 2H), 7.39 (d, J=8.0 Hz, 2H), 7.46-7.42 (m, 2H), 7.76-7.71 (m, $^3$H)

$^{13}$C NMR (125 MHz, CDCl$_3$) δ 24.6, 29.3, 47.0, 47.9, 63.3, 63.7, 67.3, 72.6, 106.9, 114.1, 118.8, 123.2, 124.0, 126.5, 126.7, 126.9, 127.8, 128.3, 129.8, 134.6, 136.6, 137.3, 137.5, 145.7, 156.5

In the following Examples 1 to 5, the same compounds which fall in the scope of the present invention are prepared using different methods.

<Example 1> Preparation of Solid Precursor 1a mmol/g, 10.0 g, 42 mmol). The reaction mixture was stirred at 0° C. for 6 hr, and then cautiously filtered using a Buchner funnel, and the polymer collected in the funnel was washed several times using dimethylformamide. Washing was performed sequentially using water, acetone, tetrahydrofuran and acetone, and drying under reduced pressure was carried out, thus obtaining a desired compound, that is, propargyloxymethyl polystyrene (2a, 10.78 g). The peak of acetylene was observed at 3287 cm$^{-1}$ using IR spectroscopy.

Step 2: Preparation of Solid Compound 4a

Acetonitrile (10 mL) was placed in a reactor containing the polymer 2a (1.00 g) obtained in Step 1, and the azido compound 3a (2.03 g, 5.82 mmol) obtained in Preparation Example 2, copper iodide (148 mg, 0.78 mmol), and diisopropylethylamine (0.203 mL, 1.17 mmol) were sequentially added, after which the resulting mixture was reacted overnight at mom temperature. The polymer was separated through a filter, washed sequentially using acetone, methanol, 10% triethylamine/dichloromethane, dichloromethane and n-hexane, and then dried under reduced pressure, thus obtaining a desired compound, that is, a polymer 4a (2.26 g). It was confirmed that 1.45 mmol/g of the 1,2,3-triazole sulfonate group was contained based on the nitrogen content using elemental analysis and that the terminal acetylene peak at 3287 cm$^{-1}$ disappeared using IR spectroscopy.

Step 3: Preparation of Solid Precursor 1a

Acetonitrile (8.0 mL) was added to a reactor containing the polymer 4a (2.20 g, 3.61 mmol) obtained in Step 2, and methyl trifluoromethanesulfonate (MeOTf, 0.8 mL, 7.22 mmol) was added, after which the resulting mixture was

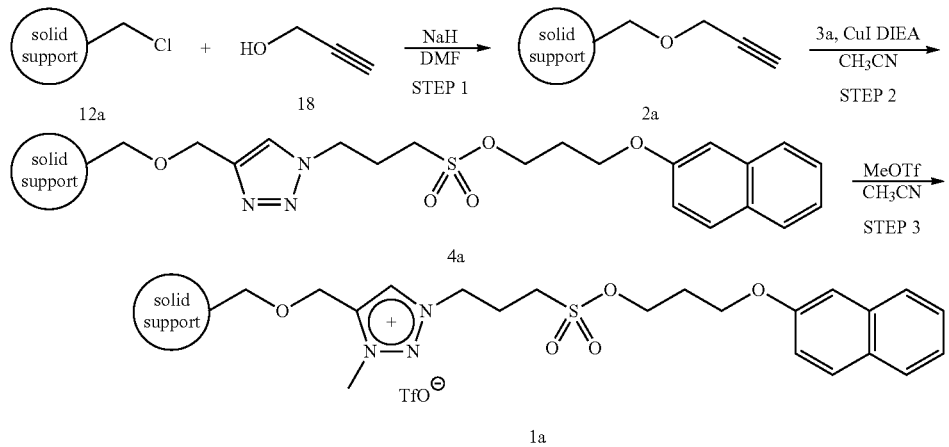

Step 1: Preparation of Solid Compound 2a

Propargyl alcohol (18, 7.335 mL, 126 mmol) was cautiously added at 0° C. to anhydrous dimethylformamide (100 mL) containing 60% sodium hydride (NaH, 5.04 g, 126 mmol) under nitrogen. The reaction mixture was stirred at 0° C. for 30 min, and then added with well-dried 4-(chloromethyl)polystyrene (12a, 100-200 mesh; Cl content: 4.2 reacted at mom temperature for 6 hr. The polymer was filtered through a filter, washed sequentially using acetonitrile, acetone and dichloromethane, and then dried under reduced pressure, thus obtaining a desired compound, that is, a solid precursor 1a (2.31 g, 83%). Using IR spectroscopy, strong bands due to the trifluoromethanesulfonate anion were observed at 1252, 1155 and 1027 cm$^{-1}$.

<Example 2> Preparation of Solid Precursor 1b

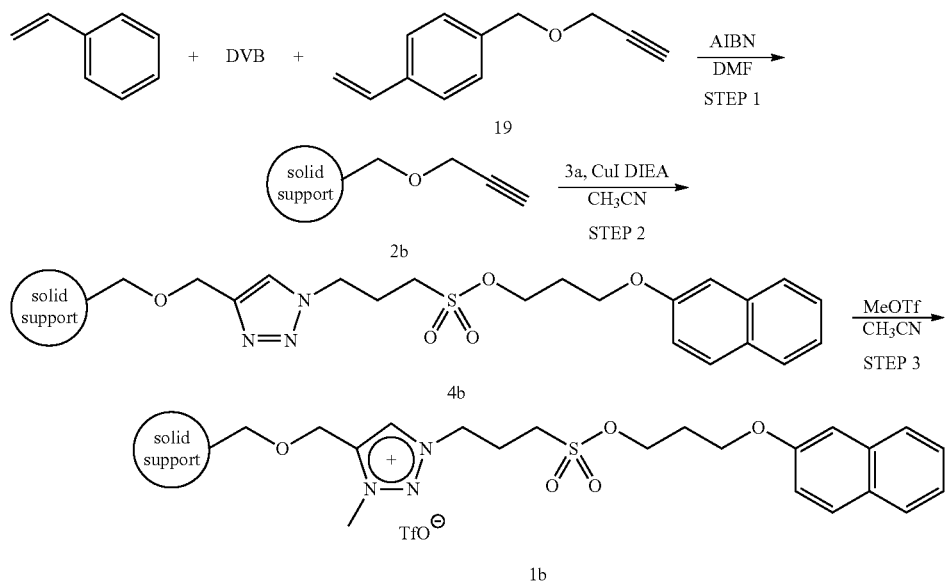

Step 1: Preparation of Solid Compound 2b 4-vinylbenzyl propargyl ether (19, 2.054 g, 12.8 mmol) obtained in Preparation Example 1, styrene (1.47 mL, 12.8 mmol), divinylbenzene (DVB, 3.65 mL, 25.6 mmol), and AIBN (azobisisobutyronitrile) (421 mg, 3.85 mmol) were dissolved in dimethylformamide (21 mL) and then reacted at 80° C. for 6 hr. The produced solid was ground to a sand size using a mortar and then washed well with acetone. The washed product was dried in air, finely ground again using a mortar, and sorted to different sizes using sieves, thus obtaining a desired compound 2b (5.8 g, 87%). Using IR spectroscopy, the peak of acetylene was observed at 3301 cm$^{-1}$.

Step 2: Preparation of Solid Compound 4b

Acetonitrile (10 mL) was placed in a reactor containing the polymer 2b (1.70 g) obtained in Step 1, and the azido compound 3a (1.7 g, 4.87 mmol) obtained in Preparation Example 2, copper iodide (124 mg, 0.65 mmol), and diisopropylethylamine (0.17 mL, 0.98 mmol) were sequentially added, after which the resulting mixture was reacted overnight at mom temperature. The polymer was separated through a filter, washed sequentially using acetone, methanol, 10% triethylamine/dichloromethane, dichloromethane and n-hexane, and then dried under reduced pressure, thus obtaining a desired compound, that is, a polymer 4b (1.82 g). It was confirmed that 0.90 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1b

Acetonitrile (8.0 mL) was added to a reactor containing the polymer 4b (1.70 g, 1.53 mmol) obtained in Step 2, and methyl trifluoromethanesulfonate (MeOTf, 0.495 mL, 4.22 mmol) was added, after which the resulting mixture was reacted overnight at mom temperature. The polymer was filtered through a filter, washed sequentially using acetonitrile, acetone and dichloromethane, and then dried under reduced pressure, thus obtaining a desired compound, that is, a polymer 1b (2.06 g). Using IR spectroscopy, strong bands due to the trifluoromethanesulfonate anion were observed at 1257, 1164 and 1030 cm$^{-1}$.

<Example 3> Preparation of Solid Precursor 1c

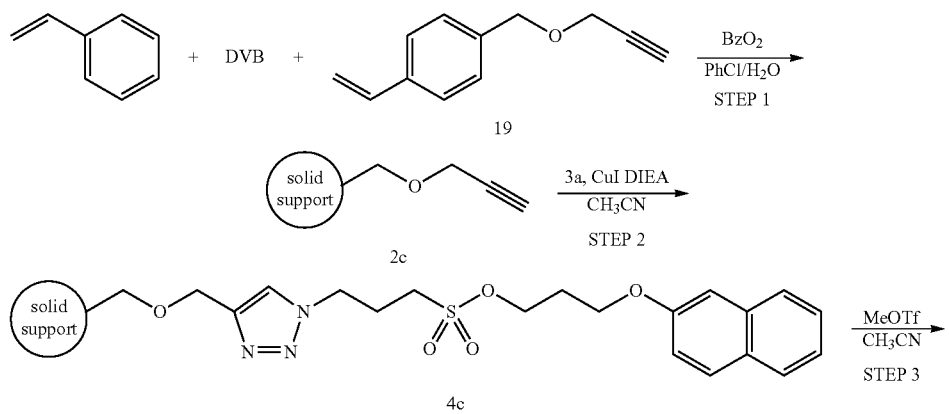

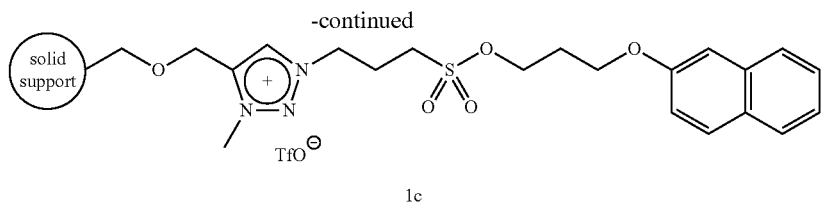

1c

Step 1: Preparation of Solid Compound 2c

*Acacia* gum (40 g) and sodium chloride (10 g) were dissolved in distilled water (1 L) and filtered using a Celite filter. The filtrate was placed in a vessel equipped with a mechanical stirrer, and rapidly stirred at a rate of 500~600 r.p.m., after which a solution of 4-vinylbenzyl propargyl ether (19, 13.0 g, 75.5 mmol) obtained in Preparation Example 1, styrene (8.2 g, 78.6 mmol), divinylbenzene (DVB, 12.4 g, 95.5 mmol), and benzoyl peroxide {(BzO)$_2$, 3.08 g, 9.55 mmol} dissolved in monochlorobenzene (PhCl, 120 mL) was rapidly added. The resulting mixture was stirred at 500~600 r.p.m. for about 5 min, and the temperature was gradually increased to 90° C. and the stirring rate was decreased to 250~300 r.p.m. Reaction overnight and then cooling were performed, and the produced polymer resin was filtered using a 400 mesh sieve, washed several times using hot water, and then washed several times using acetone. The polymer resin was transferred into a soxhlet device, heated to reflux overnight using a tetrahydrofuran solvent and washed. The polymer resin was taken out from the soxhlet device, washed with n-hexane, and then dried under reduced pressure. 32.0 g (95%) of the dried polymer resin 2c was sorted to different sizes using 50, 100, 200, and 400 mesh sieves. The peak of acetylene was observed at 3285 cm$^{-1}$ using IR spectroscopy.

Step 2: Preparation of Solid Compound 4c

Acetonitrile (10 mL) was placed in a reactor containing the solid compound 2c (1.00 g) obtained in Step 1, and the azido compound 3a (1.57 g, 4.50 mmol) obtained in Preparation Example 2, copper iodide (43 mg, 0.21 mmol), and diisopropylethylamine (0.12 mL, 0.68 mmol) were sequentially added, after which the resulting mixture was reacted overnight at room temperature. The polymer was separated through a filter, washed sequentially using acetone, methanol, 10% triethylamine/dichloromethane, dichloromethane and n-hexane, and then dried under reduced pressure, thus obtaining a desired compound, that is, a polymer 4c (1.82 g). It was confirmed that 1.23 mmol/g of the 1,2,3-triazole sulfonate group was contained based on the nitrogen content using elemental analysis and that the terminal acetylene peak at 3285 cm$^{-1}$ disappeared using IR spectroscopy.

Step 3: Preparation of Solid Precursor 1c

Acetonitrile (2.0 mL) was added to a reactor containing the solid compound 4c (300 mg, 0.372 mmol) obtained in Step 2, and methyl trifluoromethanesulfonate (MeOTf, 0.085 mL, 0.756 mmol) was added, after which the resulting mixture was reacted overnight at room temperature. The solid compound was filtered through a filter, washed sequentially using acetonitrile, acetone and dichloromethane, and then dried under reduced pressure, thus obtaining a desired compound, that is, a solid precursor 1c (336 mg, 93%). It was confirmed that 1.06 mmol/g of the 1,2,3-triazolium sulfonate group was contained based on the nitrogen content using elemental analysis and that strong bands due to the trifluoromethanesulfonate anion were observed at 1256, 1158 and 1029 cm$^{-1}$ using IR spectroscopy.

<Example 4> Preparation of Solid Precursor 1d

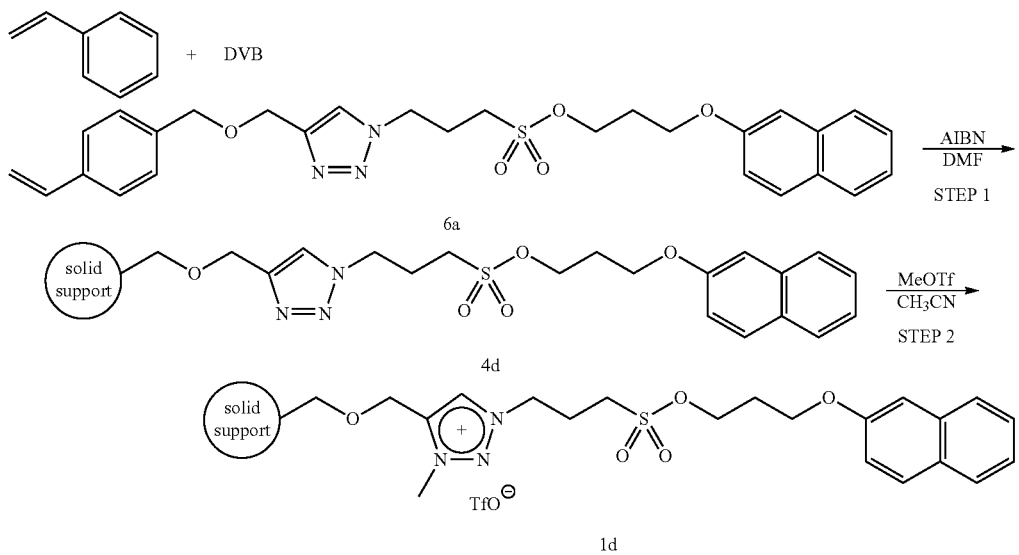

Step 1: Preparation of Solid Compound 4d

The compound 6a (1.0 g, 1.917 mmol) obtained in Preparation Example 3, styrene (292 mg, 1.917 mmol), divinylbenzene (DVB, 0.546 mL, 3.834 mmol), and AIBN (63 mg, 0.3834 mmol) were dissolved in dimethylformamide (6 mL) and then reacted at 80° C. for 6 hr. The produced solid was ground to a sand size using a mortar and then washed well with acetone. The washed product was dried in air, finely ground again using a mortar, and sorted to different sizes using sieves, thus obtaining a desired compound 4d (0.948 g, 53%: 100-200 mesh, 0.470 mg; 200-400 mesh, 0.302 mg; 400 mesh or more, 176 mg).

Step 2: Preparation of Solid Precursor 1d

Acetonitrile (5.0 mL) was placed in a reactor containing the solid compound 4d (470 mg, 0.503 mmol) obtained in Step 1, and methyl trifluoromethanesulfonate (MeOTf, 0.114 mL, 1.01 mmol) was added, after which the resulting mixture was reacted overnight at room temperature. The solid compound was filtered through a filter, washed sequentially using acetonitrile, acetone and dichloromethane, and then dried under reduced pressure, thus obtaining a desired compound, that is, a solid precursor 1d (628 mg, 95%). It was confirmed that 0.57 mmol/g of the 1,2,3-triazolium sulfonate group was contained based on the nitrogen content using elemental analysis and that strong bands due to the trifluoromethanesulfonate anion were observed at 1257, 1158 and 1028 $cm^{-1}$ using IR spectroscopy.

<Example 5> Preparation of Solid Precursor 1e $^1$H NMR (400 MHz, $CD_3CN$) δ2.25 (quintet, J=6.1 Hz, 2H), 2.35-2.45 (m, 2H), 3.28-3.34 (m, 2H), 4.10 (s, 3H), 4.21 (t, J=5.9 Hz, 2H), 4.46 (t, J=6.1 Hz, 2H), 4.55-4.61 (m, 4H), 4.67 (s, 2H), 5.27 (dd, J=11.0, 1.2, Hz, 1H), 5.82 (dd, J=17.6, 0.8 Hz, 1H), 6.76 (dd, J=17.6, 11.0 Hz, 1H), 7.16 (dd, J=9.0, 2.4 Hz, 1H), 7.27 (d, J=2.4 Hz, 1H), 7.30-7.38 (m, 3H), 7.42-7.48 (m, 3H), 7.72-7.83 (m, 3H), 8.25 (s, 1H)

$^{13}$C NMR (100 MHz, $CD_3CN$) δ24.7, 30.0, 39.5, 47.0, 52.8, 60.5, 64.8, 69.3, 73.9, 108.1, 115.3, 120.0, 122.1 (q, J=318 Hz, 1C), 125.1, 127.6, 127.8, 128.1, 128.9, 129.8, 130.2, 130.7, 130.8, 135.9, 137.6, 138.0, 138.8, 142.1, 157.9.

Step 2: Preparation of Solid Precursor 1e

The compound 7a (1.00 g, 1.458 mmol) obtained in Step 1, styrene (222 mg, 1.458 mmol), divinylbenzene (DVB, 0.415 mL, 2.916 mmol), and AIBN (48 mg, 0.292 mmol) were dissolved in dimethylformamide (6 mL) and then reacted at 80° C. for 6 hr. The produced solid was ground to a sand size using a mortar and then washed well with acetone. The washed product was dried in air, finely ground again using a mortar, and sorted to different sizes using sieves, thus obtaining a desired compound, that is, a solid

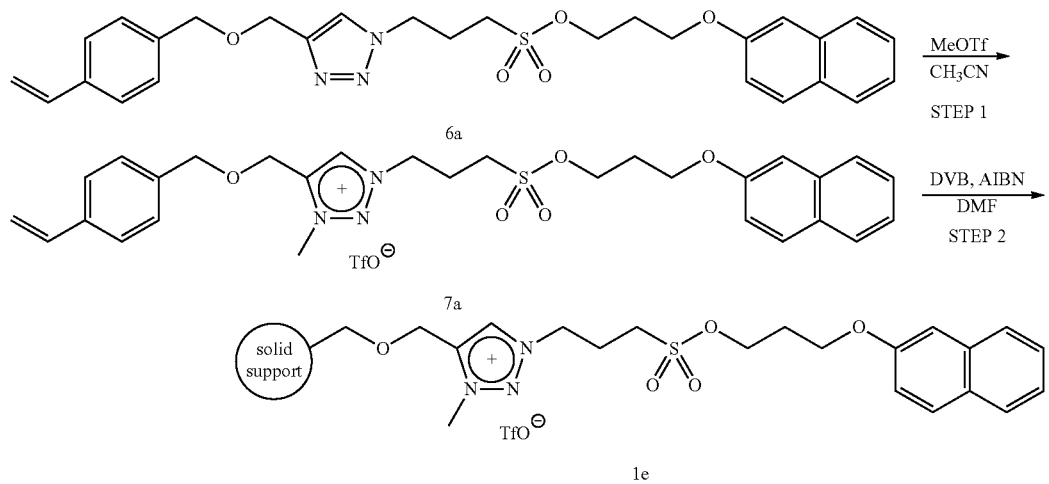

Step 1: Preparation of Compound 7a

The compound 6a (800 mg, 1.53 mmol) obtained in Preparation Example 3 was dissolved in acetonitrile (20 mL), after which methyl trifluoromethanesulfonate (MeOTf, 0.225 mL, 1.99 mmol) was added at mom temperature, and the resulting mixture was stirred for 3 hr. The reaction mixture was concentrated under reduced pressure, thus obtaining a desired compound 7a (1.05 g, 100%).

precursor 1e (1.40 g, 87%). It was confirmed that 0.89 mmol/g of the 1,2,3-triazolium sulfonate group was contained based on the nitrogen content using elemental analysis and that strong bands due to the trifluoromethanesulfonate anion were observed at 1257, 1160 and 1030 $cm^{-1}$ using IR spectroscopy.

<Example 6> Preparation of Solid Precursor 1f

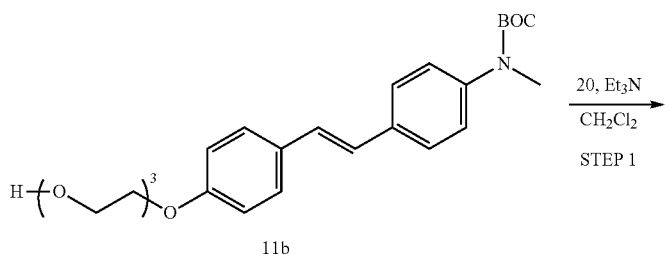

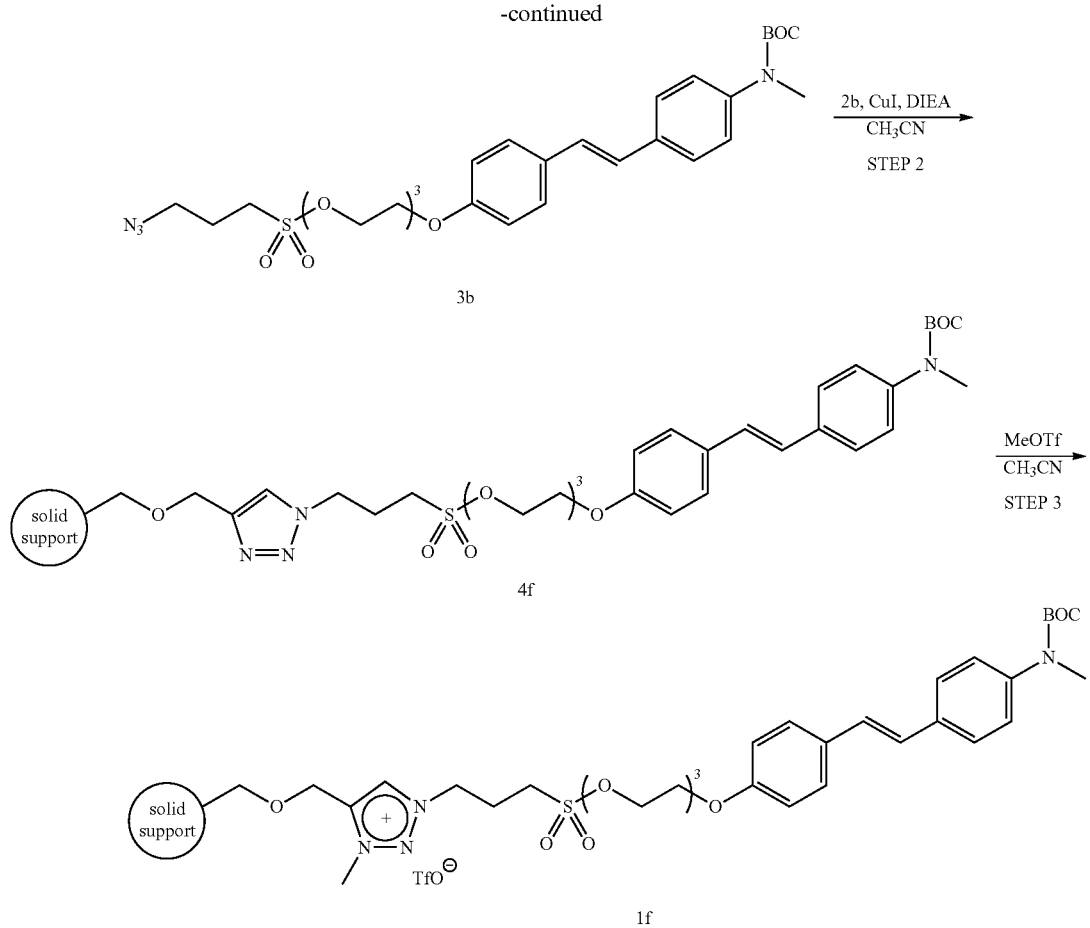

Step 1: Preparation of Compound 3b

A compound 11b (500 mg, 1.09 mmol) was dissolved in dichloromethane (15 mL), sequentially mixed with 3-azidopropane sulfonate (20, 221 mg, 1.20 mmol) and triethylamine (0.228 mL, 1.64 mmol) at 0° C., and then stirred at 0° C. for 30 min. Water was added to the reaction mixture so that reaction was terminated, and the organic compound was extracted with dichloromethane, after which the organic layer was treated with anhydrous sodium sulfate and then subjected to column chromatography (3% methanol/dichloromethane), thus obtaining a desired compound 3b (600 mg, 91%).

$^1$H NMR (500 MHz, CDCl$_3$) δ 1.46 (s, 9H), 2.10 (quintet, J=6.88 Hz, 2H), 3.24-3.27 (m, 5H), 3.47 (t, J=6.5 Hz, 2H), 3.69-3.74 (m, 4H), 3.76-3.74 (m, 2H), 3.86 (t, J=4.8 Hz, 2H), 4.15 (t, J=9.0 Hz, 2H), 4.37-4.39 (m, 2H), 6.91 (d, J=9.0 Hz, 2H), 6.95 (d, J=16.5 Hz, 1H), 7.01 (d, J=16.5 Hz, 1H), 7.21 (d, J=8.5 Hz, 2H), 7.44 (d, J=7.5 Hz, 4H)

$^{13}$C NMR (125 MHz, CDCl$_3$) δ 23.7, 28.5, 37.4, 47.7, 49.5, 67.7, 69.2, 69.4, 70.0, 70.8, 70.9, 71.0, 80.5, 115.0, 125.7, 126.3, 126.5, 127.9, 128.1, 130.6, 134.8, 143.0, 154.9, 158.6

Step 2: Preparation of Solid Compound 4f

Acetonitrile (2 mL) was placed in a reactor containing the solid compound 2b (200 mg) obtained in Step 1 of Example 2, and the compound 3b (345 mg, 0.570 mmol) obtained in Step 1 as above, copper iodide (5 mg, 0.027 mmol), and diisopropylethylamine (0.014 mL, 0.08 mmol) were sequentially added, after which the resulting mixture was reacted overnight at room temperature. The solid compound was separated through a filter, washed sequentially using acetone, methanol, 10% triethylamine/dichloromethane, dichloromethane and n-hexane, and then dried under reduced pressure, thus obtaining a desired compound, that is, a solid compound 4f (423 mg). It was confirmed that 0.94 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1f

Acetonitrile (2.0 mL) was placed in a reactor containing the solid compound 4f (230 mg, 0.219 mmol) obtained in Step 2, and methyl trifluoromethanesulfonate (MeOTf, 0.050 mL, 0.439 mmol) was added, after which the resulting mixture was reacted overnight at room temperature. The polymer was separated through a filter, washed sequentially using acetonitrile, acetone and dichloromethane, and then dried under reduced pressure, thus obtaining a desired compound, that is, a solid precursor 1f (252 mg, 95%). It was confirmed that 0.84 mmol/g of the 1,2,3-triazolium sulfonate group was contained based on the nitrogen content using elemental analysis and that strong bands due to the trifluoromethanesulfonate anion were observed at 1249, 1151 and 1029 cm$^{-1}$ using IR spectroscopy.

<Example 7> Preparation of Solid Precursor 1g

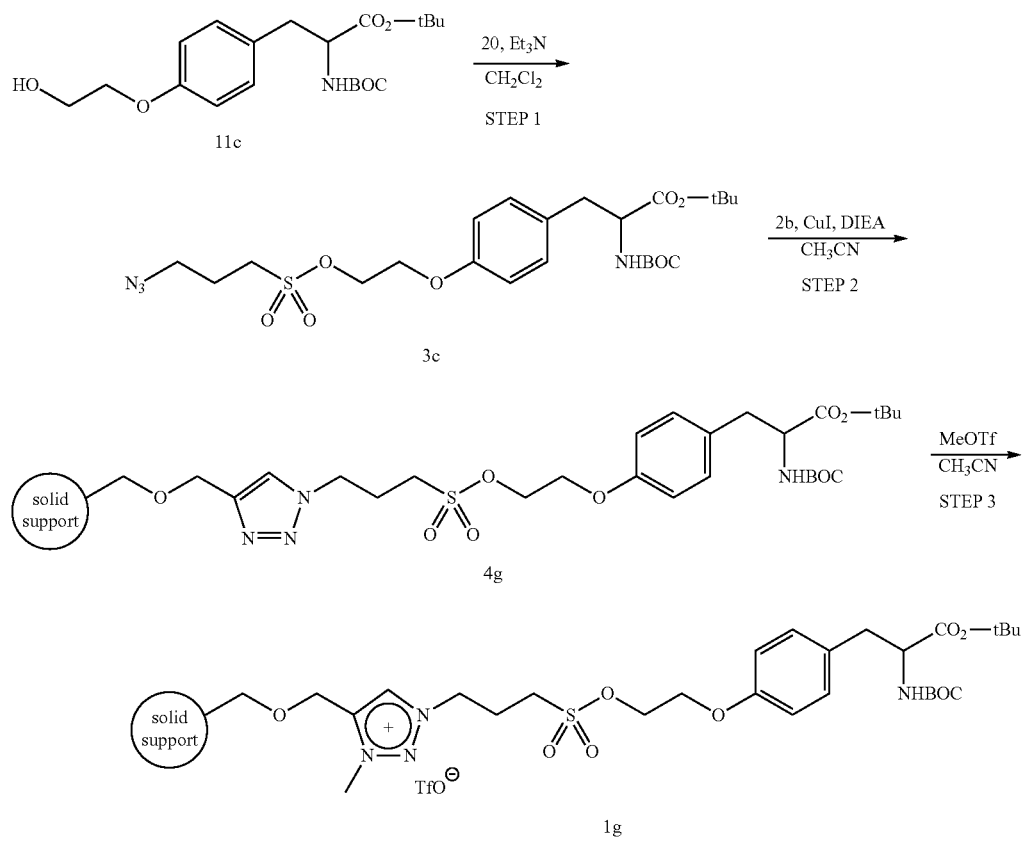

Step 1: Preparation of Compound 3c

A compound 3c (127 mg, 92%) was obtained in the same manner as in Preparation Example 2, with the exception that a compound 11c (100 mg, 0.26 mmol) was used.

$^1$H NMR (400 MHz, CDCl$_3$) δ1.08 (s, 9H), 2.10 (quintet, J=6.9 Hz, 2H), 2.56 (d, J=9.6 Hz, 1H), 2.76 (dd, J=13.5, 5.6 Hz, 1H), 2.85 (dd, J=13.6, 6.8 Hz, 1H), 3.27 (t, J=7.2 Hz, 2H), 3.44 (t, J=6.4 Hz, 2H), 3.47-3.49 (m, 1H), 4.21 (t, J=4.4 Hz, 2H), 4.56 (t, J=4.4 Hz, 2H), 6.38 (d, J=8.4 Hz, 2H), 7.13-7.17 (m, 5H), 7.20-7.25 (m, 6H), 7.43-7.45 (m, 6H)

$^{13}$C NMR (100 MHz, CDCl$_3$) δ23.5, 27.9, 41.1, 47.7, 49.2, 57.9, 65.8, 68.2, 71.2, 80.5, 114.8, 126.3, 127.8, 128.8, 131.0, 131.3, 146.3, 156.7, 173.5.

Step 2: Preparation of Solid Compound 4g

A solid compound 4g (160 mg, 96%) was obtained in the same manner as in Step 2 of Example 6, with the exception that the solid compound 2b (83 mg) obtained in Step 1 of Example 2 and the compound 3c (100 mg, 0.189 mmol) obtained in Step 1 as above were used. It was confirmed that 0.95 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1g

A solid precursor 1g (180 mg, 98%) was obtained in the same manner as in Step 3 of Example 6, with the exception that the solid compound 4g (150 mg, 0.14 mmol) obtained in Step 2 was used. It was confirmed that 0.86 mmol/g of the 1,2,3-triazolium sulfonate group was contained based on the nitrogen content using elemental analysis and that strong bands due to the trifluoromethanesulfonate anion were observed at 1249, 1151 and 1029 cm$^{-1}$ using IR spectroscopy.

<Example 8> Preparation of Solid Precursor 1 h

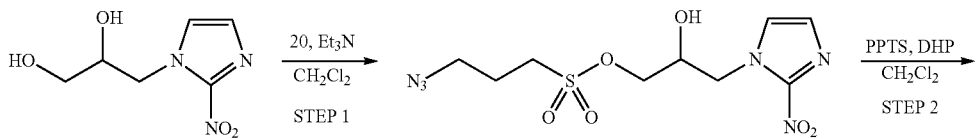

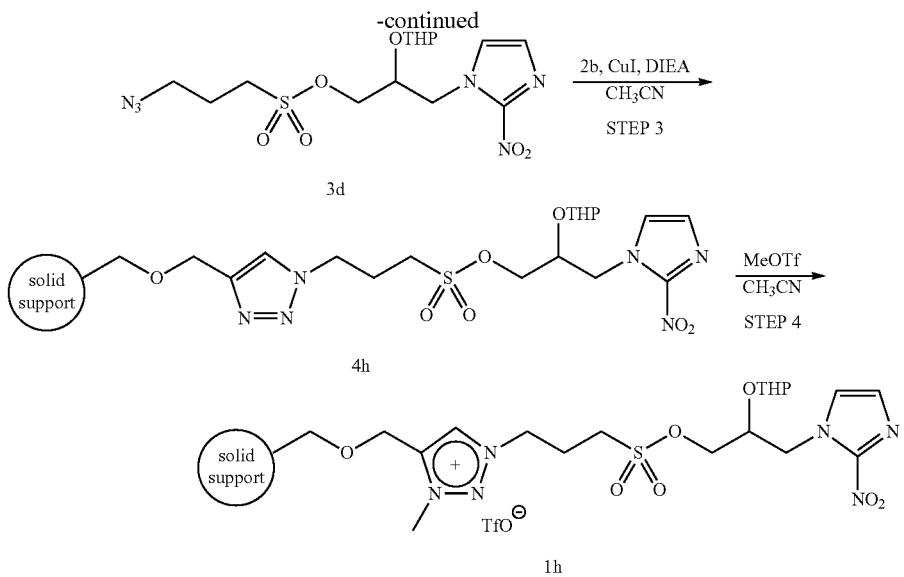

Step 1: Preparation of Compound 22

A compound 22 (1.285 g, 72%) was obtained in the same manner as in Preparation Example 2, with the exception that a compound 21 (1.00 g, 5.34 mmol) was used.

$^1$H NMR (400 MHz, CD$_3$OD) δ2.07 (quintet, J=7.1 Hz, 2H), 3.34-3.38 (m, 2H), 3.49 (t, J=6.6 Hz, 2H), 4.19-4.28 (m, 3H), 4.43 (dd, J=13.8, 8.2 Hz, 1H), 4.71 (dd, J=14.0, 3.6 Hz, 1H), 4.85 (s, 1H), 7.12 (d, J=1.2 Hz, 1H), 7.45 (d, J=1.2 Hz, 1H)

$^{13}$C NMR (100 MHz, CD$_3$OD) δ23.1, 46.7, 49.0, 51.5, 67.5, 70.5, 105.0, 126.8, 127.8

Step 2: Preparation of Compound 3d

The compound 22 (1.00 g, 2.99 mmol) obtained in Step 1 was dissolved in dichloromethane (20 mL), mixed with pyridinium para-toluene sulfonate (PPTS, 150 mg, 0.60 mmol) and 3,4-dihydropyran (DHP, 0.465 mL, 4.485 mmol), and stirred overnight at mom temperature. The reaction solution was concentrated under reduced pressure and then separated using column chromatography, yielding a compound 3d (diastereomeric mixture, 1.00 g, 80%).

$^1$H NMR (400 MHz, CDCl$_3$) δ1.37-1.76 (m, 6H), 2.10-2.20 (m, 2H), 3.12-3.17 (m, 0.5H), 3.28-3.35 (m, 2.5H), 3.43-3.49 (m, 0.5H), 3.52-3.57 (m, 2H), 3.84-3.90 (m, 0.5; H), 4.16-4.21 (m, 0.5H), 4.24-4.29 (m, 1H), 4.33-4.39 (m, 0.5H), 4.41-4.43 (m, 1.5H), 4.44-4.48 (m, 0.5; H), 4.56 (dd, J=14.0, 8.4 Hz, 0.5H), 4.69-4.70 (m, 0.5H), 4.77 (dd, J=14.0, 3.6 Hz, 0.5H), 4.84 (dd, J=14.0, 3.2 Hz, 0.5H), 7.15 (d, J=1.2 Hz, 0.5H), 7.16 (d, J=0.8 Hz, 0.5H), 7.21 (d, J=0.8 Hz, 0.5H), 7.26 (d, J=0.8 Hz, 0.5H)

$^{13}$C NMR (100 MHz, CDCl$_3$) δ14.2, 19.4, 19.9, 21.0, 23.3, 23.4, 24.8, 24.9, 30.1, 30.7, 47.4, 47.7, 49.1, 49.2, 50.6, 50.9, 60.4, 62.8, 63.9, 67.0, 69.0, 70.8, 74.9, 97.1, 101.6, 127.3, 127.8, 127.9, 128.2, 144.9, 171.1

Step 3: Preparation of Solid Compound 4h

A solid compound 4h (752 mg, 95%) was obtained in the same manner as in Step 2 of Example 6, with the exception that the solid compound 2b (0.50 g, 0.76 mmol) obtained in Step 1 of Example 2 and the compound 3d (0.50 g, 1.19 mmol) obtained in Step 2 as above were used. It was confirmed that 0.99 mmol/g of the 1,2,3-triazole sulfonate group was contained based on the nitrogen content using elemental analysis and that the terminal acetylene peak at 3301 cm$^{-1}$ disappeared using IR spectroscopy.

Step 4: Preparation of Solid Precursor 1h

A solid precursor 1h (698 mg, 100%) was obtained in the same manner as in Step 3 of Example 6, with the exception that the solid compound 4h (600 mg, 0.59 mmol) obtained in Step 3 was used. It was confirmed that 0.84 mmol/g of the 1,2,3-triazolium sulfonate group was contained based on the nitrogen content using elemental analysis and that strong bands due to the trifluoromethanesulfonate anion were observed at 1248, 1150 and 1027 cm$^{-1}$ using IR spectroscopy.

<Example 9> Preparation of Solid Precursor 1i

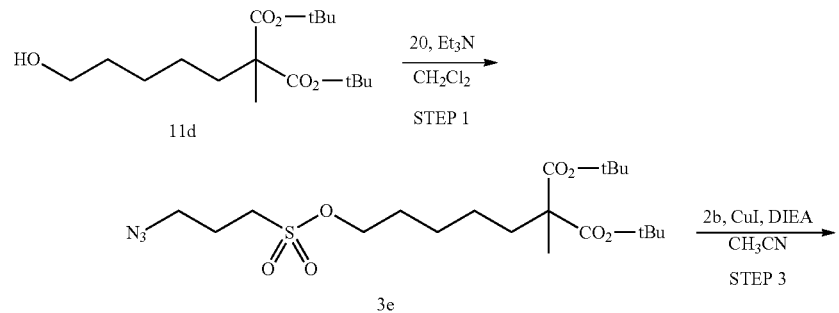

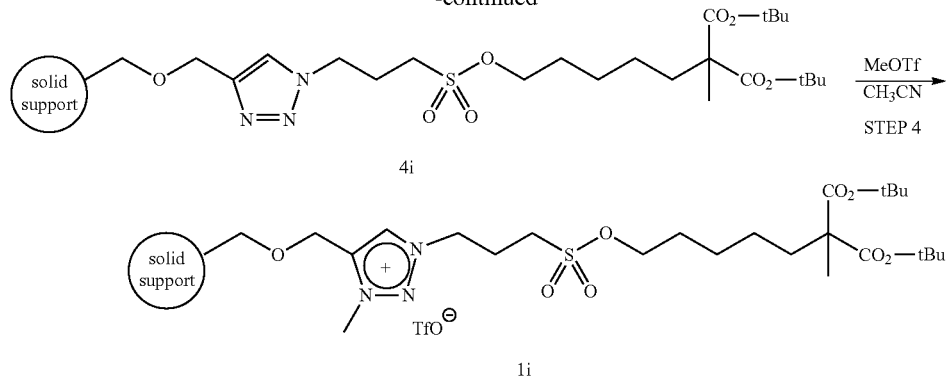

4i

1i

Step 1: Preparation of Compound 3e

A compound 11d (320 mg, 1.01 mmol) was dissolved in dichloromethane (5 mL), and 3-azidopropanesulfonyl chloride (20, 223 mg, 1.21 mmol) was added, after which triethylamine (0.211 mL, 1.52 mmol) was slowly added at 0° C. The reaction mixture was stirred at room temperature for 1 hr and then concentrated under reduced pressure, and the produced precipitate was filtered, washed with ethylacetate and subjected to column chromatography (40% ethylacetate/n-hexane), yielding a desired compound 3e (460 mg, 98%).

$^1$H NMR (400 MHz, CDCl$_3$) δ1.26-1.30 (m, 2H), 1.31 (s, 3H), 1.39-1.43 (m, 2H), 1.45 (s, 18H), 1.75-1.79 (m, 4H), 2.11 (quintet, J=6.9 Hz, 2H), 3.19 (t, J=7.4 Hz, 2H), 3.52 (t, J=6.4 Hz, 2H), 4.23 (t, J=6.4 Hz, 2H)

$^{13}$C NMR (100 MHz, CDCl$_3$) δ19.7, 23.5, 23.6, 25.8, 27.9, 29.0, 35.1, 47.3, 49.3, 54.4, 69.9, 81.0, 171.7

Step 2: Preparation of Solid Compound 4i

A solid compound 4i (750 mg, 89%) was obtained in the same manner as in Step 2 of Example 6, with the exception that the solid compound 2b (0.52 g, 0.57 mmol) obtained in Step 1 of Example 2 and the compound 3e (400 mg, 0.86 mmol) obtained in Step 1 as above were used. It was confirmed that 0.73 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1i

A solid precursor 1i (792 mg) was obtained in the same manner as in Step 3 of Example 6, with the exception that the solid compound 4i (700 mg, 0.53 mmol) obtained in Step 2 was used. It was confirmed that 0.64 mmol/g of the 1,2,3-triazolium sulfonate group was contained based on the nitrogen content using elemental analysis and that strong bands due to the trifluoromethanesulfonate anion were observed at 1249, 1152 and 1028 cm$^{-1}$ using IR spectroscopy.

<Example 10> Preparation of Solid Precursor 1j

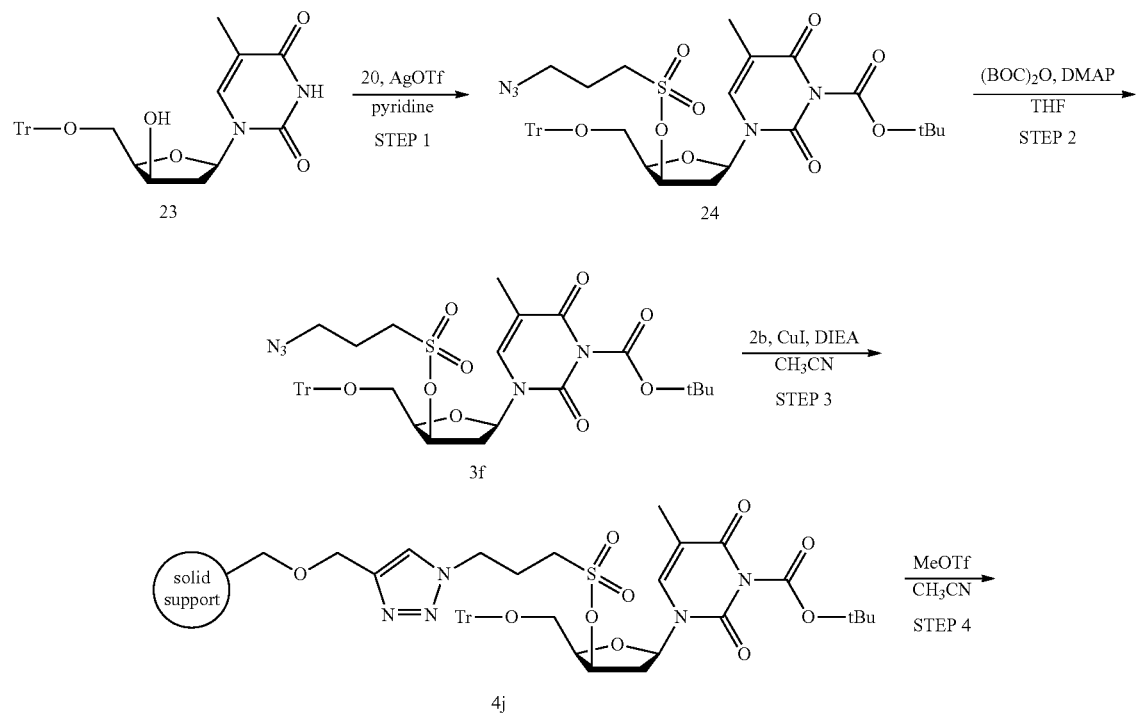

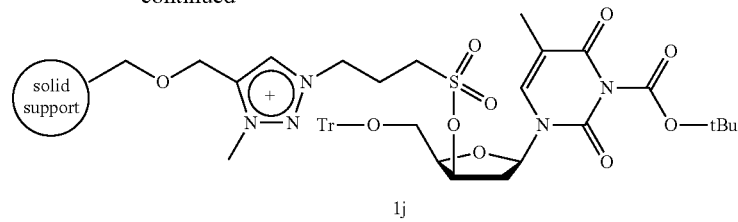

1j

Step 1: Preparation of Compound 24

A compound 23 (1.00 g, 1.95 mmol) and silver trifluoromethanesulfonate (AgOTf, 530 mg, 2.06 mmol) were dissolved in pyridine (20 mL), and 3-azidopropanesulfonyl chloride (20, 393 mg, 2.14 mmol) was slowly added at 0° C., and the resulting mixture was stirred overnight at room temperature. The reaction product was added with water and then extracted with ethylacetate, and the organic layer was washed with a 2N hydrochloric acid aqueous solution, treated with anhydrous sodium sulfate and then subjected to column chromatography (80% ethylacetate/n-hexane), thus obtaining a desired compound 24 (770 mg, 71%).

$^1$H NMR (200 MHz, CDCl$_3$) δ 1.92-1.71 (m, 5H), 2.53-2.43 (m, 1H), 3.10-2.73 (m, 3H), 3.39-3.28 (m, 3H), 3.68-3.60 (m, 1H), 4.26-4.18 (m, 1H), 5.28 (t, J=3.8 Hz, 1H), 6.30-6.25 (m, 1H), 7.38-7.24 (m, 10H), 7.46-7.40 (m, 6H), 9.19 (s, 1H)

$^{13}$C NMR (50 MHz, CDCl$_3$) δ 12.5, 23.1, 39.6, 48.6, 48.9, 61.3, 78.6, 81.2, 83.8, 87.5, 111.2, 127.5, 128.0, 128.6, 135.1, 143.2, 150.5, 163.7

Step 2: Preparation of Compound 3f

The compound 24 (700 mg, 1.108 mmol) obtained in Step 1 was dissolved in a tetrahydrofuran (15 mL) solution, and sequentially mixed with N,N-dimethylaminopyridine (DMAP, 177 mg, 1.44 mmol) and di-tert-butyl dicarbonate ((BOC)$_2$O, 289 mg, 1.33 mmol), after which the resulting mixture was stirred at mom temperature for 1 hr. The stirred mixture was added with water and extracted with ethylacetate, and the organic layer was treated with anhydrous sodium sulfate and then subjected to column chromatography (40% ethylacetate/n-hexane), thus obtaining a desired compound 3f (803 mg, 99%).

$^1$H NMR (200 MHz, CDCl$_3$) δ 1.60 (s, 9H), 1.90-1.68 (m, 5H), 2.53-2.43 (m, 1H), 3.06-2.71 (m, 3H), 3.39-3.28 (m, 3H), 3.67-3.59 (m, 1H), 4.27-4.20 (m, 1H), 5.28-5.42 (m, 1H), 6.23 (dd, J=7.7 Hz, 2.9 Hz, 1H), 7.37-7.20 (m, 10H), 7.45-7.42 (m, 6H)

$^{13}$C NMR (50 MHz, CDCl$_3$) δ 12.5, 23.1, 27.4, 39.6, 48.5, 48.9, 61.4, 78.6, 81.4, 84.2, 86.9, 87.5, 110.8, 127.5, 128.0, 128.6, 134.5, 143.2, 147.8, 148.5, 161.1.

Step 3: Preparation of Solid Compound 4j

A solid compound 4j (850 mg) was obtained in the same manner as in Step 2 of Example 6, with the exception that the solid compound 2b (0.50 g, 0.55 mmol obtained in Step 1 of Example 2 and the compound 3f (600 mg, 0.82 mmol) obtained in Step 2 as above were used. It was confirmed that 0.58 mmol/g of the 1,2,3-triazole sulfonate group was contained based on the nitrogen content using elemental analysis and that the terminal acetylene peak at 3301 cm$^{-1}$ disappeared using IR spectroscopy.

Step 4: Preparation of Solid Precursor 1j

A solid precursor 1j (880 mg) was obtained in the same manner as in Step 3 of Example 6, with the exception that the solid compound 4j (800 mg, 0.46 mmol) obtained in Step 3 was used. It was confirmed that 0.49 mmol/g of the 1,2,3-triazolium sulfonate group was contained based on the nitrogen content using elemental analysis and that strong bands due to the trifluoromethanesulfonate anion were observed at 1248, 1151 and 1026 cm$^{-1}$ using IR spectroscopy.

<Example 11> Preparation of Solid Precursor 1k

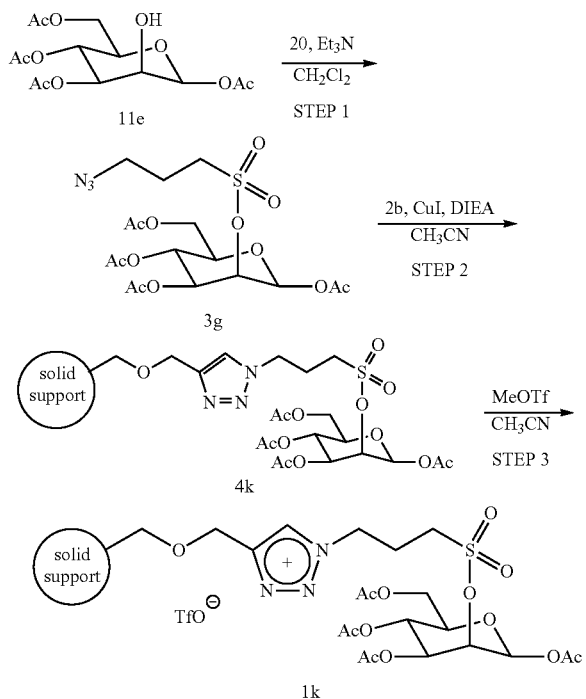

Step 1: Preparation of Compound 3g

A compound 3g (640 mg, 90%) was obtained in the same manner as in Preparation Example 2, with the exception that a compound 11e (500 mg, 1.44 mmol) was used.

$^1$H NMR (400 MHz, CDCl$_3$) δ 2.22-2.03 (m, 2H), 2.05 (s, 3H), 2.08 (s, 3H), 2.09 (s, 3H), 2.16 (s, 3H), 3.35 (t, J=7.2 Hz, 2H), 3.55 (t, J=6.0 Hz, 2H), 3.82-3.78 (m, 1H), 4.13 (dd, J=2.4, 12.4 Hz, 1H), 4.24 (dd, J=5.2, 12.4 Hz, 1H), 5.08 (d, J=2.8 Hz, 1H), 5.10 (s, 1H), 5.24 (t, J=9.6, 1H), 5.86 (s, 1H)

$^{13}$C NMR (100 MHz, CDCl$_3$) δ20.73, 20.75, 20.80, 20.84, 23.6, 49.0, 49.4, 62.0, 64.9, 70.4, 73.5, 75.0, 76.8, 77.2, 77.5, 90.1.

Step 2: Preparation of Solid Compound 4k

A solid compound 4k (1.10 g) was obtained in the same manner as in Step 2 of Example 6, with the exception that the solid compound 2b (0.74 g, 0.81 mmol) obtained in Step 1 of Example 2 and the compound 3g (600 mg, 1.21 mmol)

obtained in Step 1 as above were used. It was confirmed that 0.71 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1k

A solid precursor 1k (1.12 g) was obtained in the same manner as in Step 3 of Example 6, with the exception that the solid compound 4k (1.00 g, 0.71 mmol) obtained in Step 2 was used. It was confirmed that 0.61 mmol/g of the 1,2,3-triazolium sulfonate group was contained based on the nitrogen content using elemental analysis and that strong bands due to the trifluoromethanesulfonate anion were observed at 1255, 1158 and 1029 cm$^{-1}$ using IR spectroscopy.

<Example 12> Preparation of Solid Precursor 1l

Step 1: Preparation of Compound 3h

A compound 3h (620 mg, 85%) was obtained in the same manner as in Preparation Example 2, with the exception that a compound 11f (500 mg, 1.57 mmol) was used.

$^1$H NMR (400 MHz, CDCl$_3$) δ 2.17-2.10 (m, 2H), 3.25 (s, 3H), 3.34 (t, J=7.6 Hz, 2H), 3.51 (t, J=6.4 Hz, 2H), 4.38 (br, 1H), 4.59-4.66 (m, 4H), 5.29 (br, 1H), 7.34 (dd, J=2.8, 7.2 Hz, 1H), 7.37 (dd, J=2.8, 7.2 Hz, 1H), 7.43 (dd, J=4.8, 8.8 Hz, 1H), 7.78 (dd, J=3.2, 8.8 Hz, 1H), 7.87 (s, 1H)

$^{13}$C NMR (100 MHz, CDCl$_3$) δ 23.4, 35.9, 42.3, 47.8, 49.2, 62.2, 67.5, 119.2, 119.4, 119.9, 120.2, 123.9, 124.0, 127.8, 128.1, 128.2, 131.16, 131.23, 135.2, 136.1, 160.5, 162.3, 163.0, 165.1.

Step 2: Preparation of Solid Compound 4l

A solid compound 4l (1.10 g) was obtained in the same manner as in Step 2 of Example 6, with the exception that the solid compound 2b (0.79 g, 0.86 mmol) obtained in Step 1 of Example 2 and the compound 3h (600 mg, 1.29 mmol)

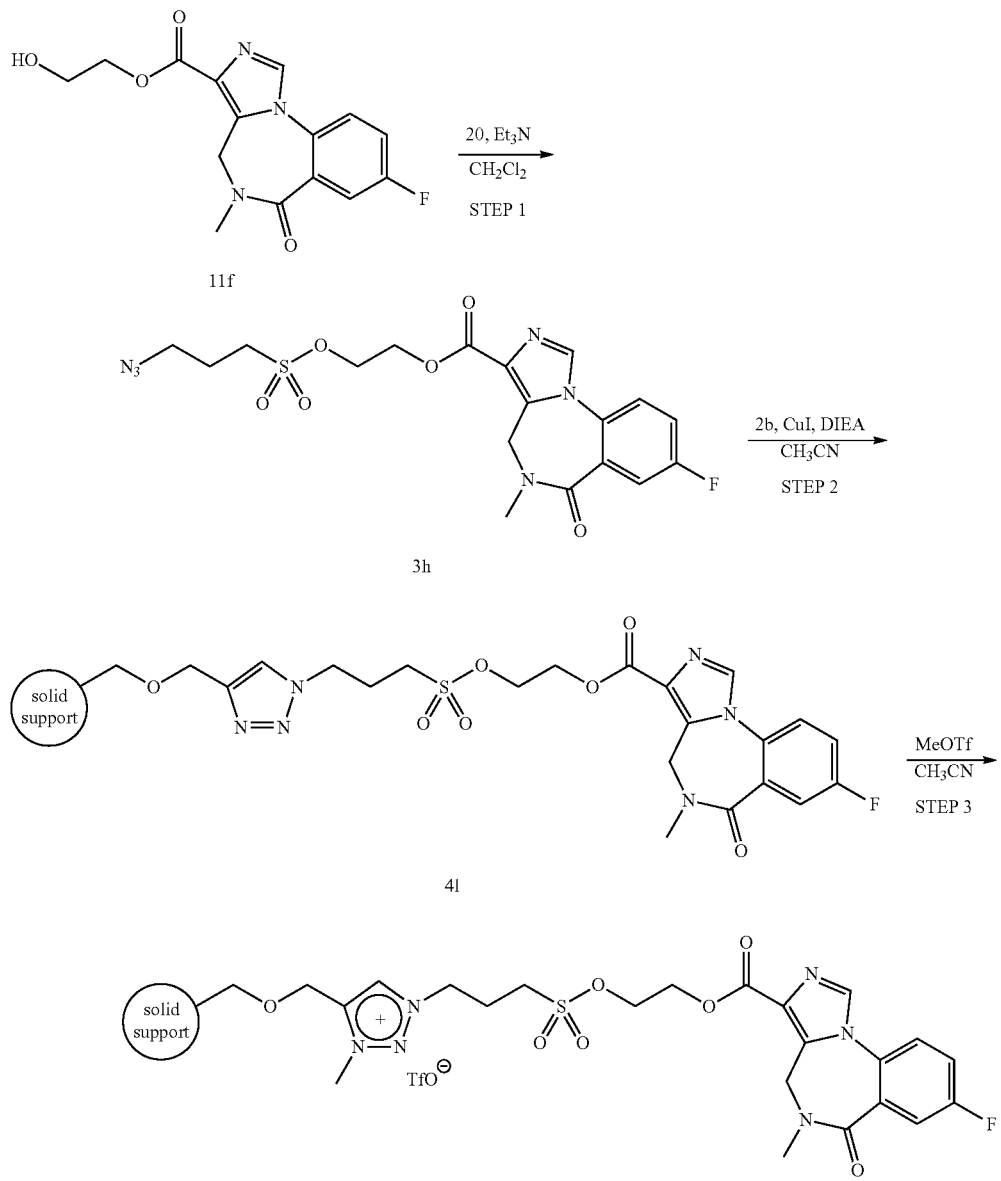

obtained in Step 1 as above were used. It was confirmed that 0.75 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1l

A solid precursor 1l (1.15 g) was obtained in the same manner as in Step 3 of Example 6, with the exception that the solid compound 4l (1.00 g, 0.75 mmol) obtained in Step 2 was used. It was confirmed that 0.64 mmol/g of the 1,2,3-triazolium sulfonate group was contained based on the nitrogen content using elemental analysis and that strong bands due to the trifluoromethanesulfonate anion were observed at 1257, 1156 and 1027 cm$^{-1}$ using IR spectroscopy.

<Example 13> Preparation of Solid Precursor 1m

J=6.8 Hz, 1H), 7.95 (d, J=7.2 Hz, 1H), 8.25 (dd, J=6.8, 2.0 Hz, 1H), 8.97 (d, J=2.0 Hz, 1H)

$^{13}$C NMR (100 MHz, CDCl$_3$) δ23.7, 28.5, 34.4, 47.8, 49.4, 68.5, 68.9, 70.5, 82.1, 105.6, 116.2, 118.5, 124.1, 125.1, 135.4, 136.4, 146.3, 149.3, 154.4, 156.5, 156.8, 163.1.

Step 2: Preparation of Compound 3i

A compound 3i (diastereomeric mixture, 577 mg, 84%) was obtained in the same manner as in Step 2 of Example 8, with the exception that the compound 26 (600 mg, 1.04 mmol) obtained in Step 1 was used.

$^1$H NMR (400 MHz, CDCl$_3$) δ1.52-1.61 (m, 3H), 1.56 (s, 9H), 1.76-1.88 (m, 3H), 2.10-2.14 (m, 2H), 3.23-3.30 (m, 2H), 3.47-3.52 (m, 2H), 3.48 (s, 3H), 3.55-3.58 (m, 1H), 3.94-3.98 (m, 1H), 4.18-4.34 (m, 3H), 4.41-4.59 (m, 2H), 4.83-4.86 (m, 1H), 7.10-7.13 (m, 1H), 7.40 (dd, J=8.0, 2.0 Hz, 1H), 7.92 (d, 7.2 Hz, 1H), 7.95 (d, J=7.2 Hz, 1H), 8.25 (dd, J=6.8, 2.0 Hz, 1H), 8.97 (d, J=1.6 Hz, 1H)

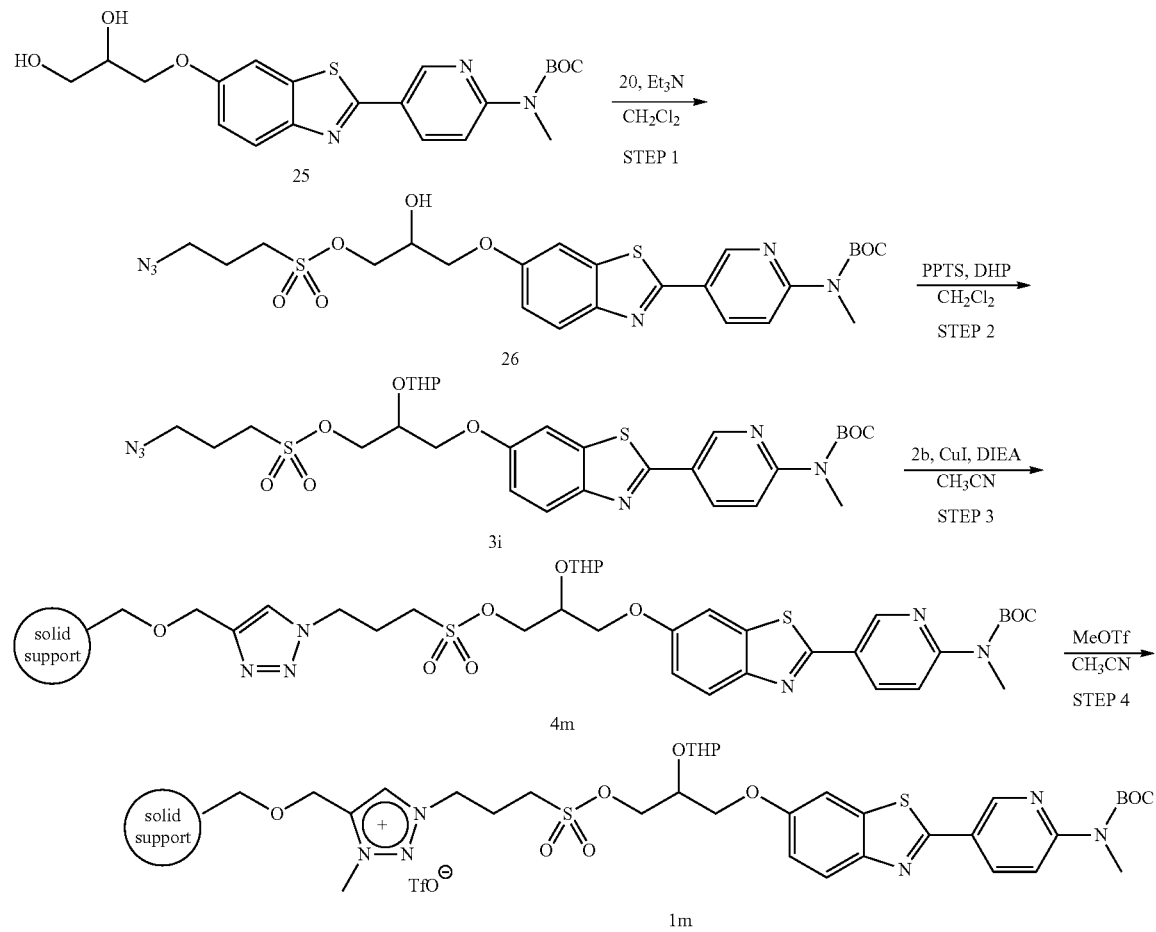

Step 1: Preparation of Compound 26

A compound 26 (675 mg, 72%) was obtained in the same manner as in Preparation Example 2, with the exception that a compound 25 (700 mg, 1.62 mmol) was used.

$^1$H NMR (400 MHz, CDCl$_3$) δ1.57 (s, 9H), 2.14 (quintet, J=5.5 Hz, 2H), 3.0 (br s, 1H), 3.31 (t, J=6.0 Hz, 2H), 3.48 (s, 3H), 3.51 (t, J=5.2 Hz, 2H), 4.15 (d, J=4.0 Hz, 2H), 4.35-4.37 (m, 1H), 4.48 (ddd, J=22.4, 8.8, 3.2 Hz, 2H), 7.11 (dd, J=7.2, 2.0 Hz, 1H), 7.37 (d, J=2.0 Hz, 1H), 7.92 (d, $^{13}$C NMR (100 MHz, CDCl$_3$) δ19.6, 19.7, 23.6, 25.3, 25.4, 28.4, 30.7, 30.8, 34.2, 47.5, 47.6, 49.35, 49.43, 63.1, 63.3, 67.2, 67.6, 68.9, 69.7, 72.8, 73.1, 81.9, 99.4, 99.5, 105.4, 105.5, 116.2, 118.4, 123.87, 123.88, 125.01, 125.03, 135.3, 136.3, 146.2, 149.0, 149.1, 154.2, 156.58, 156.59, 156.61, 156.68, 162.68, 162.74.

Step 3: Preparation of Solid Compound 4m

A solid compound 4m (0.78 g) was obtained in the same manner as in Step 2 of Example 6, with the exception that the solid compound 2b (0.46 g, 0.50 mmol) obtained in Step 1 of Example 2 and the compound 3i (500 mg, 0.75 mmol) obtained in Step 2 as above were used. It was confirmed that 0.63 mmol/g of the 1,2,3-triazole sulfonate group was contained based on the nitrogen content using elemental analysis and that the terminal acetylene peak at 3301 cm$^{-1}$ disappeared using IR spectroscopy.

Step 4: Preparation of Solid Precursor 1m

A solid precursor 1m (0.83 g) was obtained in the same manner as in Step 3 of Example 6, with the exception that the solid compound 4m (0.75 g, 0.47 mmol) obtained in Step 3 was used. It was confirmed that 0.55 mmol/g of the 1,2,3-triazolium sulfonate group was contained based on the nitrogen content using elemental analysis and that strong bands due to the trifluoromethanesulfonate anion were observed at 1259, 1157 and 1029 cm$^{-1}$ using IR spectroscopy.

<Example 14> Preparation of Solid Precursor 1n

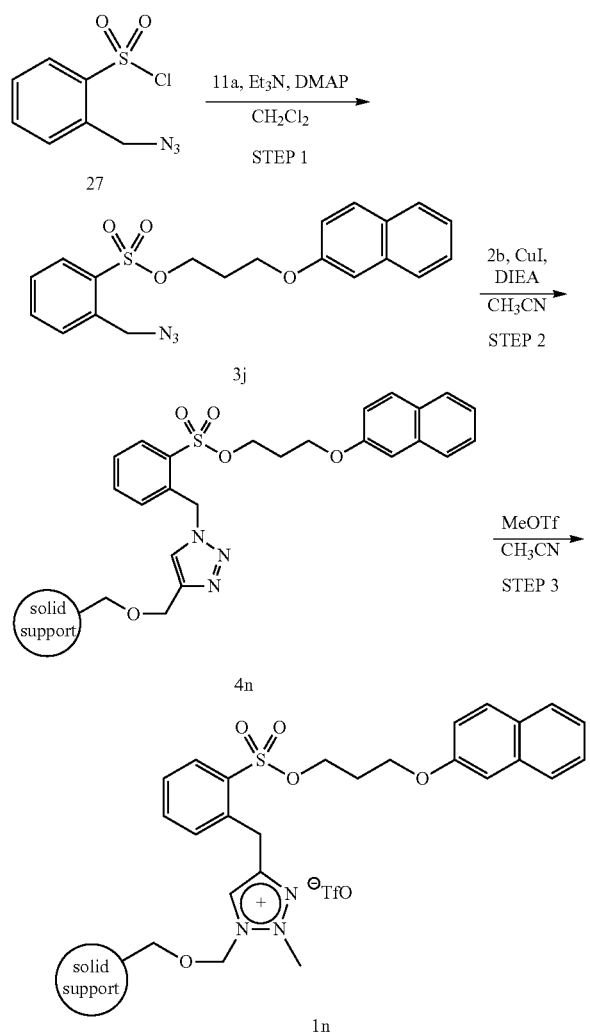

Step 1: Preparation of Compound 3j

A compound 27 (500 mg, 2.16 mmol) was dissolved in dichloromethane (20 mL), and sequentially mixed with 2-(3-hydroxypropoxy)naphthalene (11a, 470 mg, 2.37 mmol), triethylamine (0.39 mL, 2.81 mmol), and N,N-dimethylaminopyridine (DMAP, 53 mg, 0.432 mmol) at 0° C., after which the resulting mixture was stirred at 0° C. for 3 hr. Water was added to the reaction solution, the organic layer was separated, and the organic compound was extracted from the water layer using dichloromethane. The collected organic layer was concentrated under reduced pressure and then separated using column chromatography (10% ethylacetate/n-hexane), thus obtaining a desired compound 3j (472 mg, 55%) in a liquid phase.

$^1$H NMR (CDCl$_3$, 400 MHz) δ 2.22 (p, J=6.0 Hz, 2H), 4.10 (t, J=5.8 Hz, 2H), 4.32 (t, J=6.0 Hz, 2H), 4.81 (s, 2H), 7.00 (dd, J=8.8, 2.4 Hz, 1H), 7.04 (d, J=2.4 Hz, 1H), 7.34 (t, J=7.4 Hz, 1H), 7.39-7.46 (m, 2H), 7.53-7.56 (m, 2H), 7.70-7.72 (m, 2H), 7.76 (d, J=8.0 Hz, 1H), 8.01 (d, J=8.8 Hz, 1H)

$^{13}$C NMR (CDCl$_3$, 100 MHz) δ28.8, 51.2, 63.1, 67.8, 106.7, 118.5, 123.8, 126.4, 126.7, 127.6, 128.3, 129.1, 129.4, 130.1, 130.4, 133.7, 134.2, 134.4, 135.4, 156.3.

Step 2: Preparation of Solid Compound 4n

A solid compound 4n (853 mg) was obtained in the same manner as in Step 2 of Example 6, with the exception that the solid compound 2b (616 mg, 0.67 mmol) obtained in Step 1 of Example 2 and the compound 3j (400 mg, 1.01 mmol) obtained in Step 1 as above were used. It was confirmed that 0.74 mmol/g of the 1,2,3-triazole sulfonate group was contained based on the nitrogen content using elemental analysis and that the terminal acetylene peak at 3301 cm$^{-1}$ disappeared using IR spectroscopy.

Step 3: Preparation of Solid Precursor 1n

A solid precursor 1n (955 mg) was obtained in the same manner as in Step 3 of Example 6, with the exception that the solid compound 4n (850 mg, 0.63 mmol) obtained in Step 2 was used. It was confirmed that 0.63 mmol/g of the 1,2,3-triazolium sulfonate group was contained based on the nitrogen content using elemental analysis and that strong bands due to the trifluoromethanesulfonate anion were observed at 1258, 1157 and 1025 cm$^{-1}$ using IR spectroscopy.

<Example 15> Preparation of Solid Precursor 1O

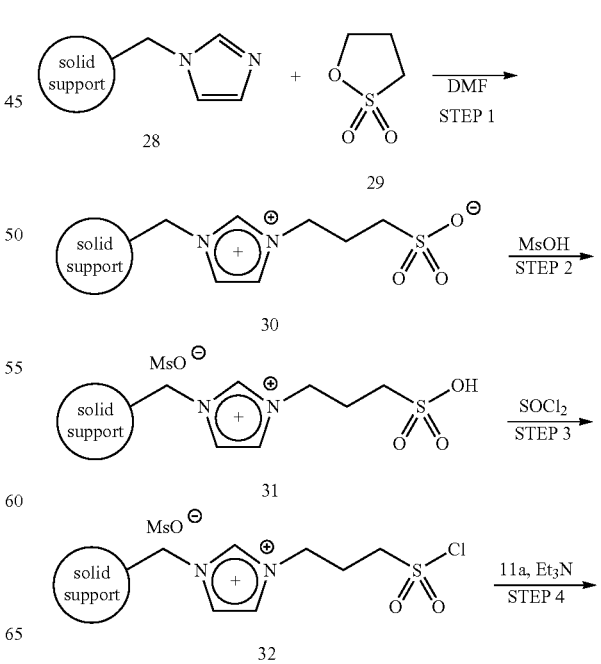

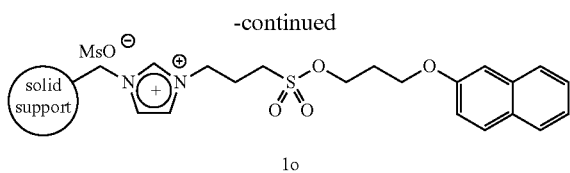

1o

Step 1: Preparation of Solid Compound 30

Dimethylformamide (10 mL) was added to a reactor containing a polystyrene resin 28 (1.00 g, 1.65 mmol) having an imidazole group so that the resin was wet, after which 1,3-propanesultone (29, 0.434 mL, 4.95 mmol) was added and the resulting mixture was then stirred at room temperature for 30 min using a vortex. The resin was filtered, washed sequentially using methanol, acetone and dichloromethane, and then dried under reduced pressure, thus obtaining a desired solid compound 30 (1.23 g). It was confirmed that 1.36 mmol/g of the imidazole group was contained based on the nitrogen content using elemental analysis and that strong sulfonate peaks were observed at 1168 and 1037 $cm^{-1}$ using IR spectroscopy.

Step 2: Preparation of Solid Compound 31

Acetonitrile (15 mL) was added to a reactor containing the solid compound 30 (1.00 g, 1.36 mmol) obtained in Step 1, and methanesulfonic acid (MsOH, 0.268 mL, 4.08 mmol) was added, after which the resulting mixture was stirred at room temperature for 24 min using a vortex. The solid compound was filtered, washed sequentially using methanol, acetone and dichloromethane, and then dried under reduced pressure, thus obtaining a desired solid compound 31 (1.29 g). Using IR spectroscopy, peaks were observed at 1338, 1222, 1166 and 1040 $cm^{-1}$.

Step 3: Preparation of Solid Compound 32

Chloroform (10 mL) was added to a reactor containing the solid compound 31 (1.00 g) obtained in Step 2, and thionyl chloride (SOCl$_2$, 0.50 mL, 6.85 mmol) was added, after which the resulting mixture was stirred at 60° C. for 3 days. The solid compound was filtered, washed sequentially using dichloromethane, acetone and dichloromethane, and then dried under reduced pressure, thus obtaining a desired solid compound 32 (0.99 g). Using IR spectroscopy, peaks were observed at 1374, 1167 and 1037 $cm^{-1}$.

Step 4: Preparation of Solid Precursor 1o

Dichloromethane (4 mL) and acetonitrile (4 mL) were added to a reactor containing the solid compound 32 (0.80 g) obtained in Step 3, and sequentially mixed with a compound 11a (303 mg, 1.50 mmol), triethylamine (0.28 mL, 2.00 mmol), and silver methane sulfonate (AgOMs, 305 mg, 1.50 mmol), after which the resulting mixture was stirred at room temperature for 2 days. The solid compound was filtered, washed sequentially using dichloromethane, acetone and dichloromethane, and then dried under reduced pressure, thus obtaining a desired solid precursor 1o (950 mg). It was confirmed that 0.87 mmol/g of the imidazolium group was contained based on the nitrogen content using elemental analysis and that peaks were observed at 1342, 1166 and 1038 $cm^{-1}$ using IR spectroscopy.

<Example 16> Preparation of Solid Precursor 1p

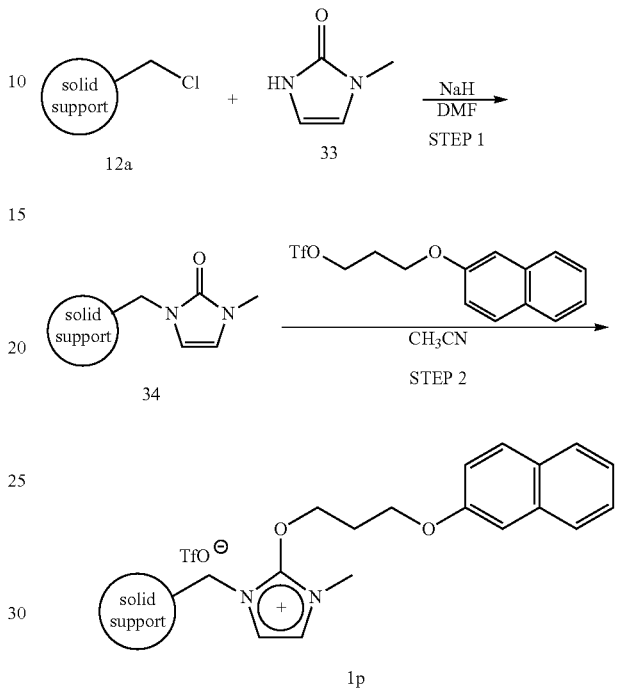

Step 1: Preparation of Solid Compound 34

A chloromethyl polystyrene resin 12a (1.00 g, 4.2 mmol) and a compound 33 (824 mg, 8.4 mmol) were placed in a reactor, anhydrous dimethylformamide (20 mL) was added, and sodium hydride (NaH, 60% in mineral oil, 504 mg, 12.6 mmol) was cautiously added. The generation of foam was stopped, and the reaction mixture was stirred overnight using a vortex. The solid compound was filtered, washed sequentially with dimethylformamide, 0.2M aqueous ammonium chloride, distilled water, methanol and tetrahydrofuran, and then dried under reduced pressure, thus obtaining a desired solid compound 34 (1.133 g). It was confirmed that 2.03 mmol/g of the 2-imidazolone compound was contained based on the nitrogen content using elemental analysis and that the strong peak was observed at 1673 $cm^{-1}$ using IR spectroscopy.

Step 2: Preparation of Solid Precursor 1p

The solid compound 34 (1.00 g, 2.03 mmol) obtained in Step 1 was placed in a reactor, mixed with a solution of compound 35 (1.003 g, 6.09 mmol) dissolved in anhydrous acetonitrile (15 mL), and stirred overnight at 60° C. The solid compound was filtered, washed sequentially with acetonitrile and dichloromethane, and then dried under reduced pressure, thus obtaining a desired solid precursor 1p (1.290 g). It was confirmed that 1.37 mmol/g of the precursor compound was contained based on the nitrogen content using elemental analysis and that strong peaks due to the trifluoromethanesulfonate anion were observed at 1599 $cm^{-1}$ and 1261, 1157 and 1030 $cm^{-1}$ using IR spectroscopy.

<Example 17> Preparation of Solid Precursor 1q

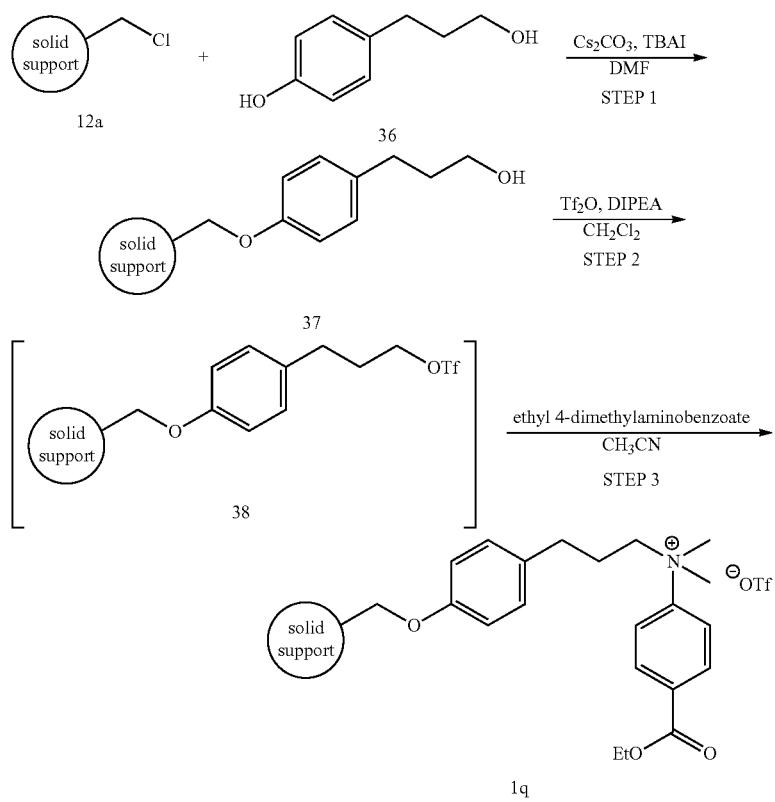

Step 1: Preparation of Solid Compound 37

A chloromethyl polystyrene resin 12a (1.00 g, 4.2 mmol), a compound 36 (1.28 g, 8.40 mmol), cesium carbonate (4.10 g, 12.6 mmol), and tetrabutylammonium iodide (TBAI, 0.77 g, 2.1 mmol) were placed in a reactor, and dimethylformamide (20 mL) was added. The reaction mixture was stirred at 60° C. for 3 hr and then cooled to room temperature, and the solid compound was filtered, washed sequentially with warm water, acetone and methanol, and then dried under reduced pressure, thus obtaining a desired solid compound 37 (1.26 g). Using IR spectroscopy, peaks were observed at 3375, 1508, 1233 and 1013 cm$^{-1}$.

Step 2: Preparation of Solid Compound 38

The polymer 37 (0.5 g) obtained in Step 1 was placed in a reactor and the reactor was filled with argon gas. Anhydrous dichloromethane (13 mL) was added so that the solid compound was wet, after which trifluoromethanesulfonic anhydride (Tf$_2$O, 0.6 mL, 6.3 mmol) and diisopropylethylamine (DIPEA, 1.46 mL, 8.4 mmol) were sequentially cautiously added, and the resulting mixture was stirred at mom temperature for 30 min. The solid compound was filtered under argon gas, washed several times with anhydrous dichloromethane solvent, and dried while allowing argon gas to flow for 5 min. The obtained solid compound 38 was used in the subsequent procedure without additional separation and analysis.

Step 3: Preparation of Solid Precursor 1q

Anhydrous acetonitrile (10 mL) in which ethyl-4-dimethylaminobenzoate (2.02 g, 10.5 mmol) was dissolved was placed in a reactor containing the solid compound 38 obtained in Step 2. The reaction mixture was stirred overnight at room temperature using a vortex, after which the solid compound was filtered, washed sequentially with acetonitrile and dichloromethane, and then dried under reduced pressure, thus obtaining a desired solid precursor 1q (0.715 g). It was confirmed that 1.60 mmol/g of the precursor was contained based on the nitrogen content using elemental analysis and that the peak at 3375 cm$^{-1}$ disappeared and peaks were observed at 1717, 1254, 1154 and 1028 cm$^{-1}$, using IR spectroscopy.

<Example 18> Preparation of Fluoride-Substituted Solid Precursor

The solid precursors (each 200 mg) of Chemical Formulas 1a~1e obtained in Examples 1~5 were placed in a frit-equipped syringe and were made wet with the addition of acetone. These precursors were washed several times with a mixture of dimethylformamide/water (2:1), washed several times with a 0.5M KF solution (dimethylformamide/water (2:1)), and washed sequentially with distilled water and acetone. The obtained solid compounds were dried under reduced pressure, yielding fluoride-substituted solid precursors. It was confirmed that strong bands due to the trifluoromethanesulfonate anion disappeared using IR spectroscopy.

<Example 19> Fluorination of Solid Precursor

Each of the fluoride-substituted solid precursors (100 mg) obtained in Example 18 was placed in a reactor, added with acetonitrile (1.0 mL) and then heated to 100° C. 0.02 mL of the reaction solution was taken out at each time of 10 min, 20 min, 40 min, 60 min, and 90 min, and diluted with acetonitrile (0.5 mL), after which the production of 2-(3-fluoropropoxy)naphthalene was measured using high-performance liquid chromatography (HPLC). The measured results are given in Table 1 below. In Table 1, the production of the 2-(3-fluoropropoxy)naphthalene in respective solid precursors was calculated on the basis of the production of 100 at 90 min.

TABLE 1

| Time (min) | 1a | 1b | 1c | 1d | 1e |
|---|---|---|---|---|---|
| 0 | 0 | 0 | 0 | 0 | 0 |
| 10 | 60 | 75 | 43 | 72 | 66 |
| 20 | 87 | 95 | 69 | 92 | 90 |
| 40 | 99 | 100 | 92 | 99 | 99 |
| 60 | 100 | 100 | 97 | 100 | 100 |
| 90 | 100 | 100 | 100 | 100 | 100 |

<Example 20> Manufacture of Cartridge Filled with Solid Precursor

Each of the solid precursors obtained in Examples 1~17 was placed in an amount of 50, 100, 200 and 300 mg in an empty cartridge equipped with fits, and the cartridge was closed with a cover, thus manufacturing the cartridge filled with the solid precursor according to the present invention. This is schematically depicted in FIG. 3.

<Example 21> 18F Fluoride Capture Test

Acetone (2.0 mL) and distilled water (2.0 mL) were allowed to sequentially flow to the cartridge filled with the solid precursor, obtained in Example 20. A 0.2M potassium bicarbonate aqueous solution (3.0 mL) was allowed to flow, and washing was performed using distilled water (2.0 mL). An [$^{18}$F]fluoride [$^{18}$O]H$_2$O solution (1-10 mCi) produced by a cyclotron was allowed to slowly flow, and then three washings were performed using distilled water (1.0 mL). The radiation dose of the solutions passed through the cartridge and the radiation dose remaining in the cartridge were measured. The results are shown in the following Table 2 [(radiation dose (%) of [$^{18}$F]fluoride captured in cartridge)].

TABLE 1

| Precursor (mg) | 1a | 1b | 1c | 1d | 1e | 1f | 1g | 1h | 1i | 1j | 1k | 1l | 1m | 1n | 1o | 1p | 1q |
|---|---|---|---|---|---|---|---|---|---|---|---|---|---|---|---|---|---|
| 50 | 85 | 90 | 82 | 78 | 91 | 89 | — | — | — | — | — | — | — | — | — | — | — |
| 100 | 94 | 97 | 95 | 89 | 98 | 96 | — | — | — | — | — | — | — | — | — | — | — |
| 200 | 95 | 99 | 97 | 93 | 99 | 99 | 99 | 97 | 97 | 94 | 98 | 99 | 99 | 94 | 99 | 97 | 95 |
| 300 | 95 | 99 | 97 | 94 | 99 | 99 | — | — | — | — | — | — | — | — | — | — | — |

<Example 22> [$^{18}$F]Fluorination Test of Solid Precursor in Reactor

Among the cartridges in which [$^{18}$F]fluoride was captured in Example 21, the cartridges in which each of the solid precursors 1a~1f was charged in an amount of 100 mg were opened, and each of the solid precursors was cautiously transferred into the reactor from the cartridge, added with acetonitrile (0.5 mL), and stirred at 100° C. for 20 min, after which the radio-TLC of the solution was measured, the solid precursor was filtered, and the radiation doses of the solid precursor and the filtrate were measured. The measured values are shown in the following Table 3 [Radio-TLC (%) of filtrate and radiation dose (%)].

TABLE 3

|  | 1a | 1b | 1c | 1d | 1e | 1f |
|---|---|---|---|---|---|---|
| Radio-TLC | 92 | 94 | 93 | 90 | 94 | 96 |
| Filtrate | 79 | 82 | 78 | 62 | 80 | 81 |
| Solid precursor | 21 | 18 | 22 | 38 | 20 | 19 |

<Example 23> [$^{18}$F] Fluorination Test in Cartridge Filled with Solid Precursor Among the cartridges in which [$^{18}$F]fluoride was captured in Example 21, the cartridges in which each of the solid precursors 1a~1q was charged in an amount of 200 mg were dewatered by allowing methanol (2.0 mL) to flow thereto, after which acetonitrile (3.0 mL) and t-amyl alcohol (3 mL) were allowed to flow, (in the case of 1q, dimethylformamide (3.0 mL) was used instead of t-amyl alcohol), and each cartridge was closed with a cover, and placed in an oil thermostatic bath at 100° C. so that the reaction was carried out for 20 min. The cartridge was taken out from the thermostatic bath and cooled, and the cover was cautiously removed from the cartridge, and acetonitrile (2.0 mL) was allowed to flow. The radio-TLC of the eluted acetonitrile solution, the radiation dose thereof, and the radiation dose remaining in the cartridge were measured. The final radio-chemical yield was determined by multiplying the radio-TLC by the radiation dose of the eluate. The results are shown in Table 4 below.

TABLE 4

| Radiation dose (%) | 1a | 1b | 1c | 1d | 1e | 1f | 1g | 1h | 1i | 1j | 1k | 1l | 1m | 1n | 1o | 1p | 1q |
|---|---|---|---|---|---|---|---|---|---|---|---|---|---|---|---|---|---|
| Radio-TLC | 95 | 98 | 99 | 92 | 98 | 99 | 97 | 95 | 99 | 83 | 63 | 93 | 97 | 97 | 99 | 91 | 99 |
| Eluate | 68 | 77 | 70 | 59 | 75 | 73 | 78 | 68 | 81 | 1 | 1 | 67 | 65 | 66 | 43 | 45 | 77 |

TABLE 4-continued

| Radiation dose (%) | 1a | 1b | 1c | 1d | 1e | 1f | 1g | 1h | 1i | 1j | 1k | 1l | 1m | 1n | 1o | 1p | 1q |
|---|---|---|---|---|---|---|---|---|---|---|---|---|---|---|---|---|---|
| Cartridge | 32 | 23 | 30 | 41 | 25 | 27 | 22 | 32 | 19 | 99 | 99 | 23 | 25 | 34 | 57 | 55 | 23 |
| Radiochemical yield | 65 | 75 | 69 | 54 | 74 | 72 | 76 | 65 | 80 | 1 | 1 | 62 | 63 | 64 | 42 | 41 | 76 |

As is apparent from Examples 18 to 23, the solid precursor according to the present invention allowed the nucleophilic fluorination to be carried out in the form of both a liquid reaction in the reactor and a solid reaction in the cartridge. Moreover, when the [$^{18}$F]fluoride solution was allowed to flow, [$^{18}$F]fluoride was efficiently captured in the cartridge (Example 21), and the [$^{18}$F]fluorination was carried out in the cartridge by virtue of simple heating (Example 23), and the produced F-18 labeled compound could be easily eluted by allowing the solution to flow after the reaction (Example 23).

The invention claimed is:

1. A solid precursor represented by Chemical Formula 1 below:

[Chemical Formula 1]

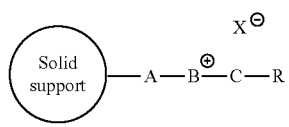

wherein the solid support is an insoluble organic polymer selected from the group consisting of polystyrene, polyacrylate, polyacrylamide, polyacrylonitrile, polyethyleneglycol and mixtures thereof, A is —$CH_2$—O—$CH_2$—,

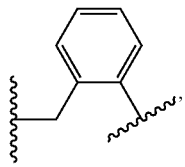 [SMILES: *Cc1ccccc1*]

—$(CH_2)_n$—, wherein n is 1~12,
B is

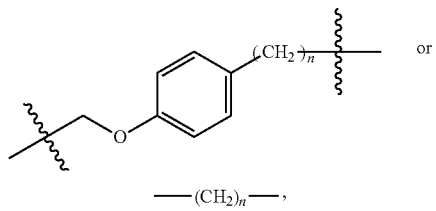

wherein $R_1$ is a $C_1$-$C_{20}$ hydrocarbon group, and the hydrocarbon group includes one or more selected from the group consisting of nitrogen, oxygen and sulfur and is unsubstituted or substituted with a halogen, and $R_4$ is a $C_1$-$C_{10}$ alkyl group, C is a single bond, —O—, or -D-$SO_2$—O—, wherein D is —$(CH_2)_n$— (n is 1~3) or

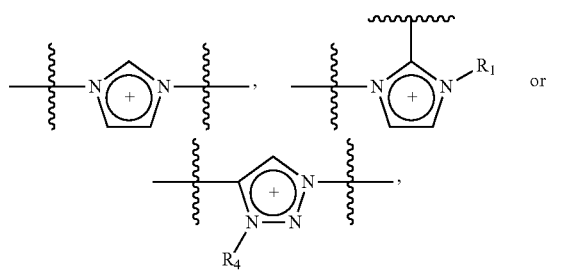

and

R is an organic group other than F-18 in an [$^{18}$F]labeled radiopharmaceutical, and hydrogen in the organic group is unsubstituted or substituted with a protecting group X is methanesulfonate, trifluoromethanesulfonate, p-nitrobenzenesulfonate, tetrafluoroborate ($BF_4$), hexafluorophosphate ($PF_6$), hexafluoroantimonate ($S_bF_6$), bis(trifluoromethane) sulfonimide($N(Tf)_2$), sodium sulfate ($NaSO_4$), potassium carbonate ($KCO_3$), bicarbonate ($HCO_3$), potassium hydrogen phosphate ($KHPO_4$), dipotassium phosphate ($K_2PO_4$) or alkane sulfonate ($R'SO_3$), wherein R' is a $C_{1-20}$ hydrocarbon group, and the $C_{1-20}$ hydrocarbon group includes one or more selected from the group consisting of nitrogen, oxygen, sulfur, phosphorus and combinations thereof and is unsubstituted or substituted with a halogen.

2. The solid precursor of claim 1, wherein R is selected from the group consisting of

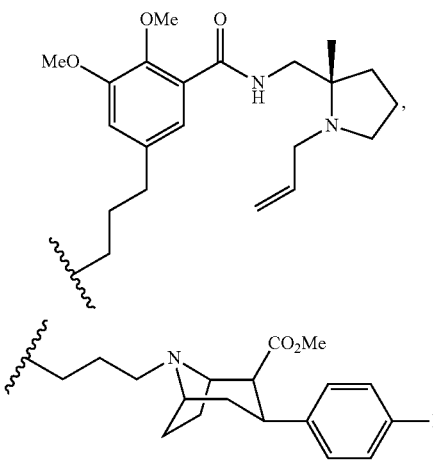

-continued

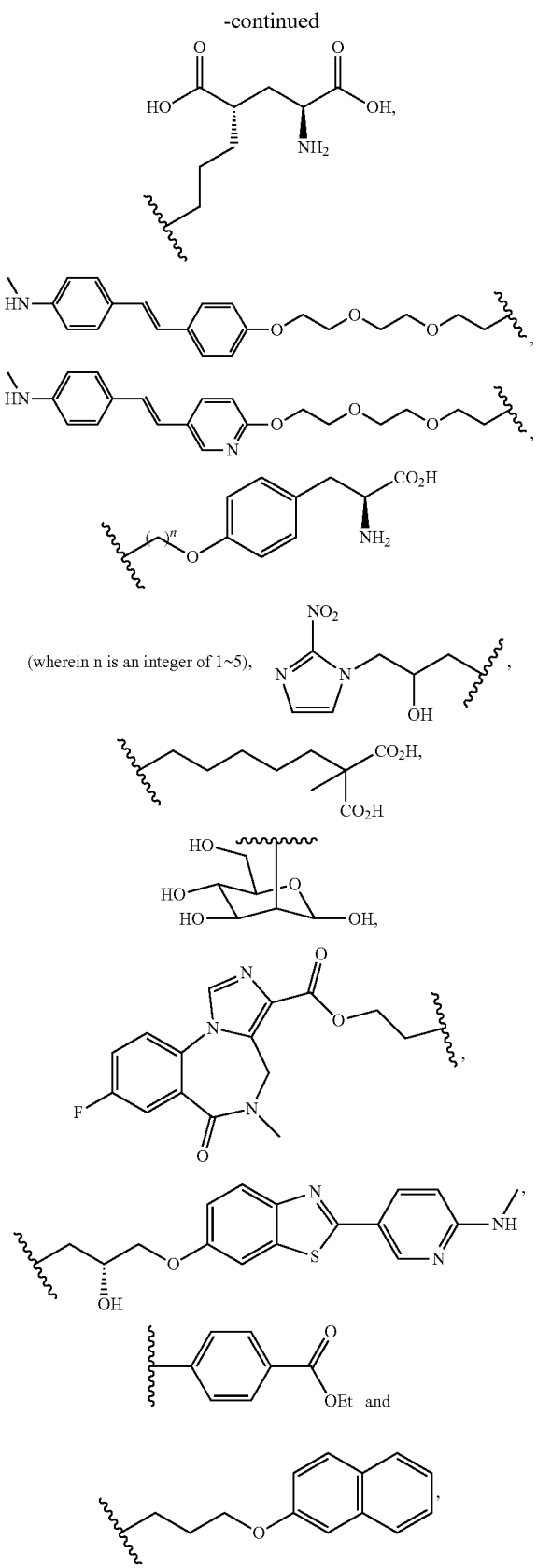

(wherein n is an integer of 1~5), wherein hydrogen is unsubstituted or substituted with a protecting group.

3. A solid precursor represented by Chemical Formula 1-4 below,

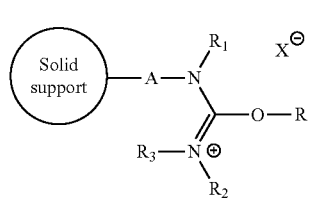

[Chemical Formula 1-4]

wherein the solid support is an insoluble organic polymer selected from the group consisting of polystyrene, polyacrylate, polyacrylamide, polyacrylonitrile, polyethyleneglycol and mixtures thereof, A is $-CH_2-O-CH_2-$,

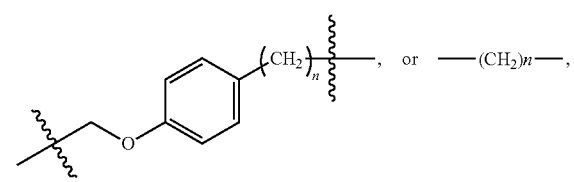, or $-(CH_2)n-$, wherein n is 1~12,

R is an organic group other than F-18 in an [$^{18}$F]labeled radiopharmaceutical, and hydrogen in the organic group is unsubstituted or substituted with a protecting group, X is methanesulfonate, trifluoromethanesulfonate, p-nitrobenzenesulfonate, tetrafluoroborate ($BF_4$), hexafluorophosphate ($PF_6$), hexafluoroantimonate ($S_bF_6$), bis(trifluoromethane) sulfonimide($N(Tf)_2$), sodium sulfate ($NaSO_4$), potassium carbonate ($KCO_3$), bicarbonate ($HCO_3$), potassium hydrogen phosphate ($KHPO_4$), dipotassium phosphate ($K_2PO_4$) or alkane sulfonate ($R'SO_3$), wherein R' is a $C_{1-20}$ hydrocarbon group, and the $C_{1-20}$ hydrocarbon group includes one or more selected from the group consisting of nitrogen, oxygen, sulfur, phosphorus and combinations thereof and is unsubstituted or substituted with a halogen, and $R_1$, $R_2$ and $R_3$ are same as or different from each other and are a $C_1$-$C_{20}$ hydrocarbon group, and the hydrocarbon group includes one or more selected from the group consisting of nitrogen, oxygen and sulfur and is unsubstituted or substituted with a halogen.

4. The solid precursor of claim 1, wherein the solid precursor of Chemical Formula 1 is represented by Chemical Formula 1-2a below,

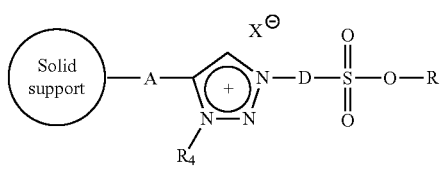

[Chemical Formula 1-2a]

wherein the solid support is an insoluble organic polymer selected from the group consisting of polystyrene, polyacrylate, polyacrylamide, polyacrylonitrile, polyethyleneglycol and mixtures thereof, A is —CH₂—O—CH₂—,

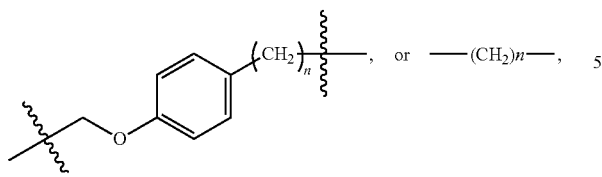, or —(CH₂)n—, wherein n is 1~12,

D is —(CH₂)ₙ— (n is 1~3) or

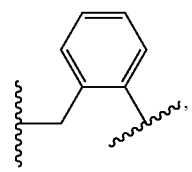 [SMILES: *Cc1ccccc1*],

R is an organic group other than F-18 in an [¹⁸F]labeled radiopharmaceutical, and hydrogen in the organic group is unsubstituted or substituted with a protecting group, X is methanesulfonate, trifluoromethanesulfonate, p-nitrobenzenesulfonate, tetrafluoroborate (BF₄), hexafluorophosphate (PF₆), hexafluoroantimonate ($S_bF_6$), bis(trifluoromethane) sulfonimide(N(Tf)₂), sodium sulfate (NaSO₄), potassium carbonate (KCO₃), bicarbonate (HCO₃), potassium hydrogen phosphate (KHPO₄), dipotassium phosphate (K₂PO₄) or alkane sulfonate (R'SO₃), wherein R' is a $C_{1-20}$ hydrocarbon group, and the $C_{1-20}$ hydrocarbon group includes one or more selected from the group consisting of nitrogen, oxygen, sulfur, phosphorus and combinations thereof and is unsubstituted or substituted with a halogen, and R₄ is a $C_{1-10}$ alkyl group.

5. The solid precursor of claim 1, wherein the solid precursor of Chemical Formula 1 is a precursor represented by Chemical Formula 1-2b below,

[Chemical Formula 1-2b]

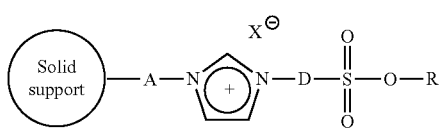

wherein the solid support is an insoluble organic polymer selected from the group consisting of polystyrene, polyacrylate, polyacrylamide, polyacrylonitrile, polyethyleneglycol and mixtures thereof, A is —CH₂—O—CH₂—,

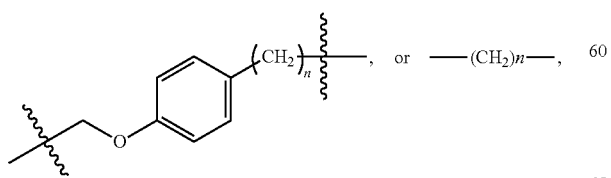, or —(CH₂)n—, wherein n is 1~12,

D is —(CH₂)ₙ— (n is 1~3) or

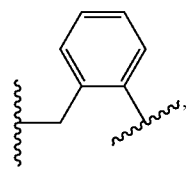 [SMILES: *Cc1ccccc1*],

R is an organic group other than F-18 in an [¹⁸F]labeled radiopharmaceutical, and hydrogen in the organic group is unsubstituted or substituted with a protecting group, X is methanesulfonate, trifluoromethanesulfonate, p-nitrobenzenesulfonate, tetrafluoroborate (BF₄), hexafluorophosphate (PF₆), hexafluoroantimonate ($S_bF_6$), bis(trifluoromethane) sulfonimide(N(Tf)₂), sodium sulfate (NaSO₄), potassium carbonate (KCO₃), bicarbonate (HCO₃), potassium hydrogen phosphate (KHPO₄), dipotassium phosphate (K₂PO₄) or alkane sulfonate (R'SO₃), wherein R' is a $C_{1-20}$ hydrocarbon group, and the $C_{1-20}$ hydrocarbon group includes one or more selected from the group consisting of nitrogen, oxygen, sulfur, phosphorus and combinations thereof and is unsubstituted or substituted with a halogen.

6. A method of preparing a solid precursor according to claim 4, as shown in the following Scheme 1, comprising:

subjecting a solid support having a terminal alkyne group represented by Chemical Formula 2 and an azidoalkane sulfonate compound represented by Chemical Formula 3 to an alkyne/azide [3+2] cycloaddition reaction using a copper (I) catalyst, thus preparing a compound connected to a solid support having a 1,2,3-triazole group represented by Chemical Formula 4 (Step 1); and subjecting 1,2,3-triazole of the compound connected to the solid support represented by Chemical Formula 4 obtained in Step 1 to alkylation, thus preparing a solid precursor having a 1,2,3-triazolium salt (Step 2);

[Scheme 1]

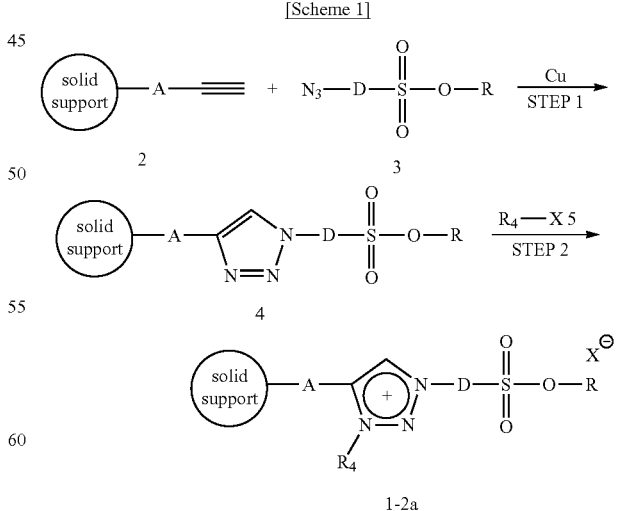

wherein the solid support, A, D, X and R are defined as

A is a linker, wherein D is a single bond or a $C_{1-30}$ hydrocarbon group,

R is an organic group other than F-18 in an [$^{18}$F]labeled radiopharmaceutical, and hydrogen in the organic group is unsubstituted or substituted with a protecting group, and X is an anion, and $R_4$ is $C_1$-$C_{10}$ alkyl group.

7. A method of preparing a solid precursor according to claim 4, as shown in the following Scheme 2, comprising:
   subjecting a 1,2,3-triazole sulfonate compound represented by Chemical Formula 6 to radical polymerization using a cross-linker and a radical initiator, thus preparing a compound connected to a solid support having a 1,2,3-triazole group represented by Chemical Formula 4 (Step 1); and
   subjecting 1,2,3-triazole of the compound connected to the solid support represented by Chemical Formula 4 obtained in Step 1 to alkylation, thus preparing a solid precursor having a 1,2,3-triazolium salt (Step 2);

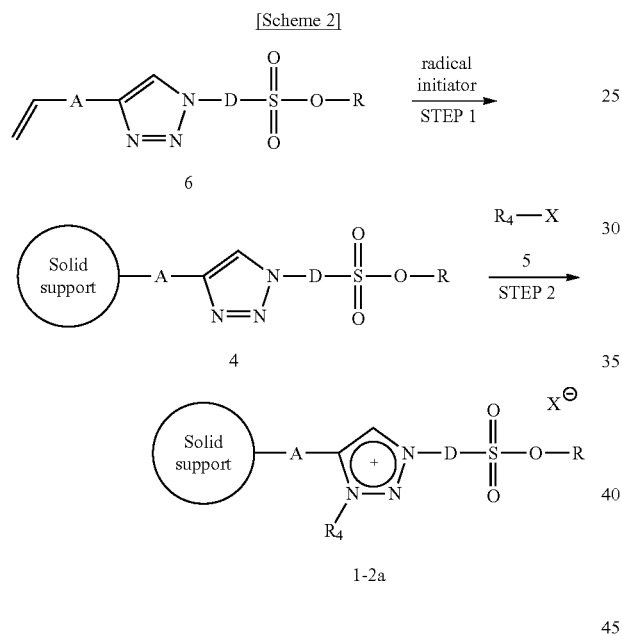

wherein the solid support, A, D, X and R are defined as
A is a linker,
wherein D is a single bond or a $C_{1-30}$ hydrocarbon group,
R is an organic group other than F-18 in an [$^{18}$F]labeled radiopharmaceutical, and hydrogen in the organic group is unsubstituted or substituted with a protecting group, and X is an anion, and $R_4$ is $C_1$-$C_{10}$ alkyl group.

8. A method of preparing a solid precursor according to claim 4, as shown in the following Scheme 3, comprising:
   subjecting a 1,2,3-triazole sulfonate compound represented by Chemical Formula 6 to alkylation, thus synthesizing a compound represented by Chemical Formula 7 having a 1,2,3-triazolium salt (Step 1); and
   subjecting the 1,2,3-triazolium sulfonate compound by Chemical Formula 7 obtained in Step 1 to radical polymerization using a cross-linker and a radical initiator, thus preparing a solid precursor having a 1,2,3-triazolium salt (Step 2);

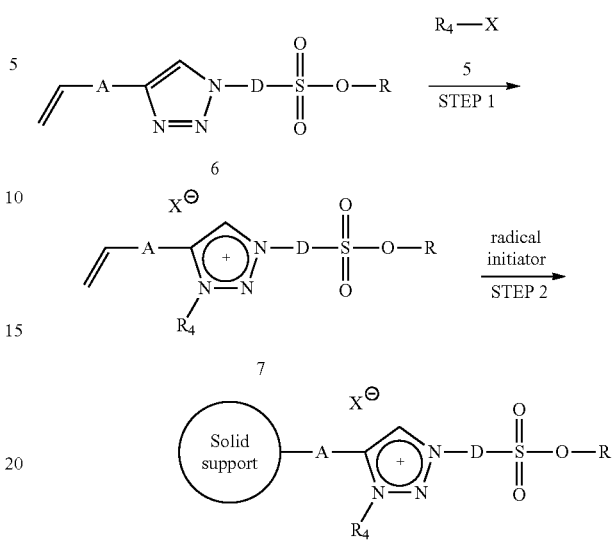

wherein the solid support, A, D, X and R are defined as
A is a linker,
wherein D is a single bond or a $C_{1-30}$ hydrocarbon group,
R is an organic group other than F-18 in an [$^{18}$F]labeled radiopharmaceutical, and hydrogen in the organic group is unsubstituted or substituted with a protecting group, and X is an anion, and $R_4$ is $C_1$-$C_{10}$ alkyl group.

9. A method of preparing a solid precursor according to claim 5, as shown in the following Scheme 4, comprising:
   reacting an imidazolium sulfonate solid compound represented by Chemical Formula 8 with an acid, thus synthesizing an imidazolium sulfonic acid solid compound represented by Chemical Formula 9 (Step 1);
   treating the solid compound represented by Chemical Formula 9 obtained in Step 1 with thionyl chloride ($SOCl_2$), thus synthesizing an imidazolium sulfonyl chloride solid compound represented by Chemical Formula 10 (Step 2); and
   reacting the solid compound represented by Chemical Formula 10 obtained in Step 2 with an alcohol compound represented by Chemical Formula 11, thus preparing a solid precursor having an imidazolium salt (Step 3);

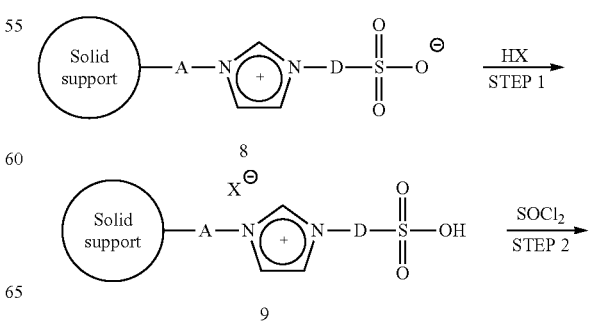

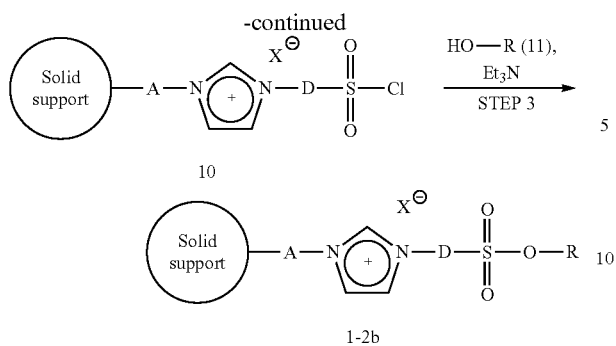

1-2b wherein the solid support, A, D, X and R are defined as

A is a linker, wherein D is a single bond or a $C_{1-30}$ hydrocarbon group,

R is an organic group other than F-18 in an [$^{18}$F]labeled radiopharmaceutical, and hydrogen in the organic group is unsubstituted or substituted with a protecting group, and X is an anion.

10. A method of preparing a solid precursor according to claim 1, as shown in the following Scheme 5, comprising:

reacting a solid compound represented by Chemical Formula 12 with a 2-imidazolone compound represented by Chemical Formula 13 under basic conditions, thus synthesizing a solid compound represented by Chemical Formula 14 (Step 1); and adding the solid compound represented by Chemical Formula 14 obtained in Step 1 with a compound 15 represented by Chemical Formula 15, thus preparing a solid precursor having an imidazolium salt (Step 2);

[Scheme 5]

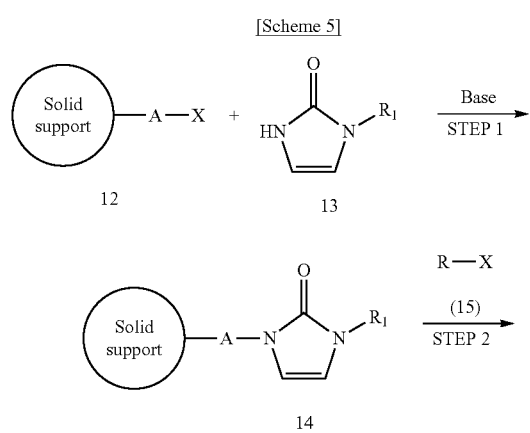

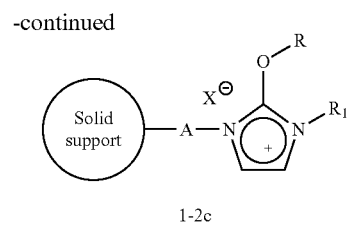

1-2c wherein the solid support, A, R and X are defined as

A is a linker,

R is an organic group other than F-18 in an [$^{18}$F]labeled radiopharmaceutical, and hydrogen in the organic group is unsubstituted or substituted with a protecting group, and X is an anion, and $R_1$ is a $C_1$-$C_{20}$ hydrocarbon group, and the hydrocarbon group includes one or more selected from the group consisting of nitrogen, oxygen and sulfur and is unsubstituted or substituted with a halogen.

11. A method of preparing a solid precursor according to claim 1, as shown in the following Scheme 6, comprising:

adding a solid compound represented by Chemical Formula 12 with a tertiary amine represented by Chemical Formula 16, thus preparing the solid precursor of Chemical Formula 1-3;

[Scheme 6]

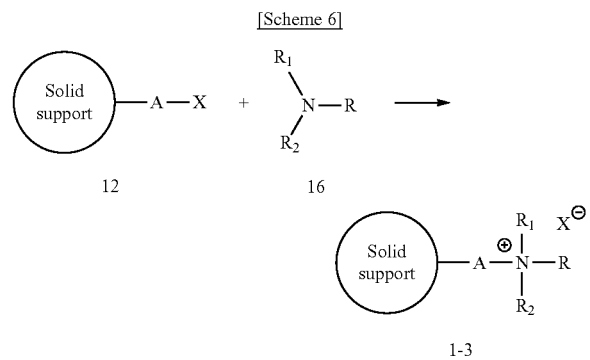

wherein the solid support, A, R and X are defined as

A is a linker,

R is an organic group other than F-18 in an [$^{18}$F]labeled radiopharmaceutical, and hydrogen in the organic group is unsubstituted or substituted with a protecting group, and X is an anion, and $R_1$ and $R_2$ are same as or different from each other and are a $C_1$-$C_{20}$ hydrocarbon group, and the hydrocarbon group includes one or more selected from the group consisting of nitrogen, oxygen and sulfur and is unsubstituted or substituted with a halogen, and the hydrocarbon group includes one or more selected from the group consisting of nitrogen, oxygen and sulfur and is unsubstituted or substituted with a halogen.

\* \* \* \* \*